US012706203B2

(12) United States Patent
Zhang et al.

(10) Patent No.: US 12,706,203 B2
(45) Date of Patent: Aug. 11, 2026

(54) CONVERSION AND TRANSFER OF REAL-TIME VOLUMETRIC IMAGE DATA FOR A MEDICAL DEVICE

(71) Applicant: Intuitive Surgical Operations, Inc., Sunnyvale, CA (US)

(72) Inventors: Hui Zhang, San Jose, CA (US); Troy K. Adebar, San Jose, CA (US); Tao Zhao, Sunnyvale, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 724 days.

(21) Appl. No.: 18/041,126

(22) PCT Filed: Aug. 6, 2021

(86) PCT No.: PCT/US2021/045092

§ 371 (c)(1),
(2) Date: Feb. 9, 2023

(87) PCT Pub. No.: WO2022/035710

PCT Pub. Date: Feb. 17, 2022

(65) Prior Publication Data

US 2023/0317252 A1 Oct. 5, 2023

Related U.S. Application Data

(60) Provisional application No. 63/063,914, filed on Aug. 10, 2020.

(51) Int. Cl.
*G16H 30/40* (2018.01)
*G06T 15/00* (2011.01)
(Continued)

(52) U.S. Cl.
CPC ............ *G16H 30/40* (2018.01); *G06T 15/00* (2013.01); *G06V 10/44* (2022.01); *G06V 10/56* (2022.01); *G16H 30/20* (2018.01)

(58) Field of Classification Search
CPC ......... G16H 20/40; G16H 50/50; G16H 40/63
See application file for complete search history.

(56) References Cited

U.S. PATENT DOCUMENTS 5,986,662 A * 11/1999 Argiro .................... G06T 11/00 345/422
6,389,187 B1 5/2002 Greenaway et al.
(Continued)

FOREIGN PATENT DOCUMENTS

EP 2669830 A1 12/2013

OTHER PUBLICATIONS

International Preliminary Report on Patentability for Application No. PCT/US2021/045092 mailed Feb. 23, 2023, 15 pages.
(Continued)

*Primary Examiner* — Michael L Burleson
(74) *Attorney, Agent, or Firm* — Haynes & Boone, LLP.

(57) ABSTRACT

A system may perform operations including receiving data comprising a plurality of image frames sampled from a volume data set of an imaged anatomical region displayable on a monitor. The plurality of image frames may correspond to a plurality of volume data reconstruction images displayed on the monitor in a series of image slices of a scrollable image stack. The operations also include analyzing the plurality of image frames to detect image features that are characteristic of a static view region in each image frame and evaluating the detected image features to determine a relative location of the detected one or more image features with respect to a scrolling view region for each image frame. The operations also include determining an
(Continued)

ordered set of the image frames sorted according to a sequence based on relative locations and producing processed video data comprising the ordered set of the image frames.

20 Claims, 12 Drawing Sheets

(51) Int. Cl.
*G06V 10/44* (2022.01)
*G06V 10/56* (2022.01)
*G16H 30/20* (2018.01)

(56) References Cited

U.S. PATENT DOCUMENTS 7,772,541 B2 8/2010 Froggatt et al.
7,781,724 B2 8/2010 Childers et al.
10,706,543 B2 7/2020 Donhowe et al.
11,202,680 B2 12/2021 Donhowe et al.
2004/0105574 A1* 6/2004 Pfaff ........................ G06T 19/00 382/128
2005/0074157 A1* 4/2005 Thomas, III ........... G16H 30/20 705/3
2005/0149041 A1* 7/2005 McGinley ............ A61B 17/155 606/88
2005/0228266 A1* 10/2005 McCombs ............ A61B 34/74 600/407
2006/0013523 A1 1/2006 Childlers et al.
2006/0093199 A1* 5/2006 Fram ...................... A61B 90/37 382/128
2007/0263915 A1* 11/2007 Mashiach ............ G06V 10/267 382/130
2009/0309874 A1* 12/2009 Salganicoff ............ A61B 6/466 345/419
2011/0295113 A1* 12/2011 Profio .................... A61B 6/032 600/425
2012/0078510 A1* 3/2012 Ma ......................... G05D 1/027 701/426
2012/0093388 A1* 4/2012 Masumoto ............ G06T 7/0012 382/134
2012/0165672 A1* 6/2012 Hill ...................... A61B 8/0883 600/443
2012/0189197 A1* 7/2012 Li ........................ H04N 9/8205 382/165
2014/0035916 A1* 2/2014 Murphy .................. G06T 15/08 345/427
2015/0313555 A1* 11/2015 Nabutovsky ........... A61B 5/316 600/374
2016/0081663 A1* 3/2016 Chen ......................... G06T 7/62 600/407
2017/0039321 A1* 2/2017 Reicher ............... G06F 3/04847
2017/0193686 A1* 7/2017 Mullins ................... G06F 3/005
2017/0266491 A1* 9/2017 Rissanen .............. G09B 19/003
2017/0371190 A1* 12/2017 Yamazaki ......... G02F 1/136286
2018/0125586 A1* 5/2018 Sela ......................... A61B 5/00
2020/0349696 A1* 11/2020 Baer-Beck .............. G06T 11/00
2021/0035302 A1* 2/2021 Cohen Maimon ...... G06T 17/00
2021/0049734 A1* 2/2021 Wahrenberg .............. G06T 5/20
2021/0145280 A1* 5/2021 Starobinets ......... G06F 3/04847
2021/0196434 A1* 7/2021 Cramer ................. G06T 7/0012
2021/0358121 A1* 11/2021 Bangia .................... G06F 18/21

OTHER PUBLICATIONS

Partial International Search Report for Application No. PCT/US21/45092 mailed on Dec. 10, 2021, 113 pages.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

MPR Visualization Image 3910

MPR Visualization Image 3920

CONVERSION AND TRANSFER OF REAL-TIME VOLUMETRIC IMAGE DATA FOR A MEDICAL DEVICE

CROSS-REFERENCE TO RELATED APPLICATION(S)

This patent application is the U.S. National Stage patent application of International Patent Application No. PCT/US2021/045092 filed on Aug. 6, 2021 which claims priority to and the benefit of U.S. Provisional Patent Application No. 63/063,914, filed Aug. 10, 2020, each of which is incorporated herein by reference in its entirety.

TECHNICAL FIELD

The present disclosure is directed to systems, devices, methods, and computer program products for transferring volumetric image data from an imaging device to a medical device.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions, an operator may insert minimally invasive medical tools to reach a target tissue location. Minimally invasive medical tools include instruments such as therapeutic, diagnostic, biopsy, and surgical instruments. Medical tools may be inserted into anatomic passageways and navigated toward a region of interest within a patient anatomy.

To assist with reaching the target tissue location, the location and movement of the minimally invasive medical tools may be mapped with image data of the patient anatomy. The image data may be used to assist navigation of the medical tools through natural or surgically-created passageways in anatomic systems such as the lungs, the colon, the intestines, the kidneys, the heart, the circulatory system, or the like. Yet, several challenges arise in reliably obtaining image data from the imaging system, particularly in real-time during medical procedures.

SUMMARY

Disclosed are devices, systems, methods and computer program products for transferring three dimensional (3D) volumetric image data collected by an imaging system as video data to a medical device in real time during a medical procedure. Implementations of the disclosed techniques can be useful for several applications of the medical device, including for example enabling updated navigation information for operating the medical device in anatomical passageways based on the transferred 3D image data. The disclosed techniques provide an alternative way to transfer 3D image data from the imaging system to the medical device without having to use and depend on the standard network for image data transfer, e.g., such as the Digital Imaging and Communications in Medicine (DICOM) standard, which may be unreliable, if even available.

In some embodiments, for example, a system for providing real-time 3D image information from an imaging system to a medical device includes a processor, and a memory coupled to the processor and storing instructions that, when executed by the processor, cause the system to perform operations comprising: receiving, at the computer device, video data comprising a plurality of image frames sampled from a 3D volume data set of an imaged anatomical region of a patient displayable on a monitor, wherein the plurality of image frames correspond to a plurality of volume data reconstruction images displayed on the monitor in a series of image slices of a scrollable image stack; implementing an optical character recognition (OCR) technique on the plurality of image frames to render text information contained in the image frames; analyzing the rendered text information to identify a constant text feature that is the same in each of the image frames and a varying text feature that is different in each of the image frames; evaluating the varying text feature in each of the image frames to create an ordered set of the image frames sorted according to a sequence based on a value of each evaluated varying text feature; and producing processed video data comprising the ordered set of the image frames.

In some embodiments, for example, a system for providing real-time 3D image information from an imaging system to a medical device includes a processor, and a memory coupled to the processor and storing instructions that, when executed by the processor, cause the system to perform operations comprising: receiving, at the computer device, video data comprising a plurality of image frames sampled from a 3D volume data set of an imaged anatomical region of a patient displayable on a monitor, wherein the plurality of image frames correspond to a plurality of volume data reconstruction images displayed on the monitor in a series of image slices of a scrollable image stack; analyzing the plurality of image frames to detect one or more image features characteristic of a static view region in each image frame where planar coordinates associated with the imaged anatomical region remain constant for each image slice in the series of image slices of the scrollable image stack; evaluating the plurality of image frames to determine a location of the one or more image features in a scrolling view region in each image frame where at least one of the planar coordinates associated with the imaged anatomical region varies for each image slice in the series of image slices of the scrollable image stack; determining an ordered set of the image frames sorted according to a sequence based on relative locations for the at least one of the planar coordinates that vary in each of the image frames; and producing processed video data comprising the ordered set of the image frames.

In some embodiments, for example, a system for providing real-time 3D image information from an imaging system to a medical device includes a processor, and a memory coupled to the processor and storing instructions that, when executed by the processor, cause the system to perform operations comprising: sampling a plurality of image frames from a 3D volume data set of an imaged anatomical region of a patient displayable on a monitor, wherein the 3D volume data set is displayable as a plurality of volume data reconstruction images in a series of image slices of a scrollable image stack; analyzing a partial region within each of the sampled image frames corresponding to the image slices of the scrollable image stack to identify one or more image features within the analyzed partial region; determining whether the one or more image features identified in the partial region changes or remains constant for each of the sampled image slices; assigning an index number to a first image frame of the sampled image frames that is different than an index number assigned to a second image frame of the sampled image frames when it is determined that the identified one or more image features has changed with respect to the first image frame and the second image frame; and producing an ordered set of the sampled image frames based on the assigned index number to create pseudo volume image data.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments depicted, but are for explanation and understanding only.

DETAILED DESCRIPTION

Figure 1:
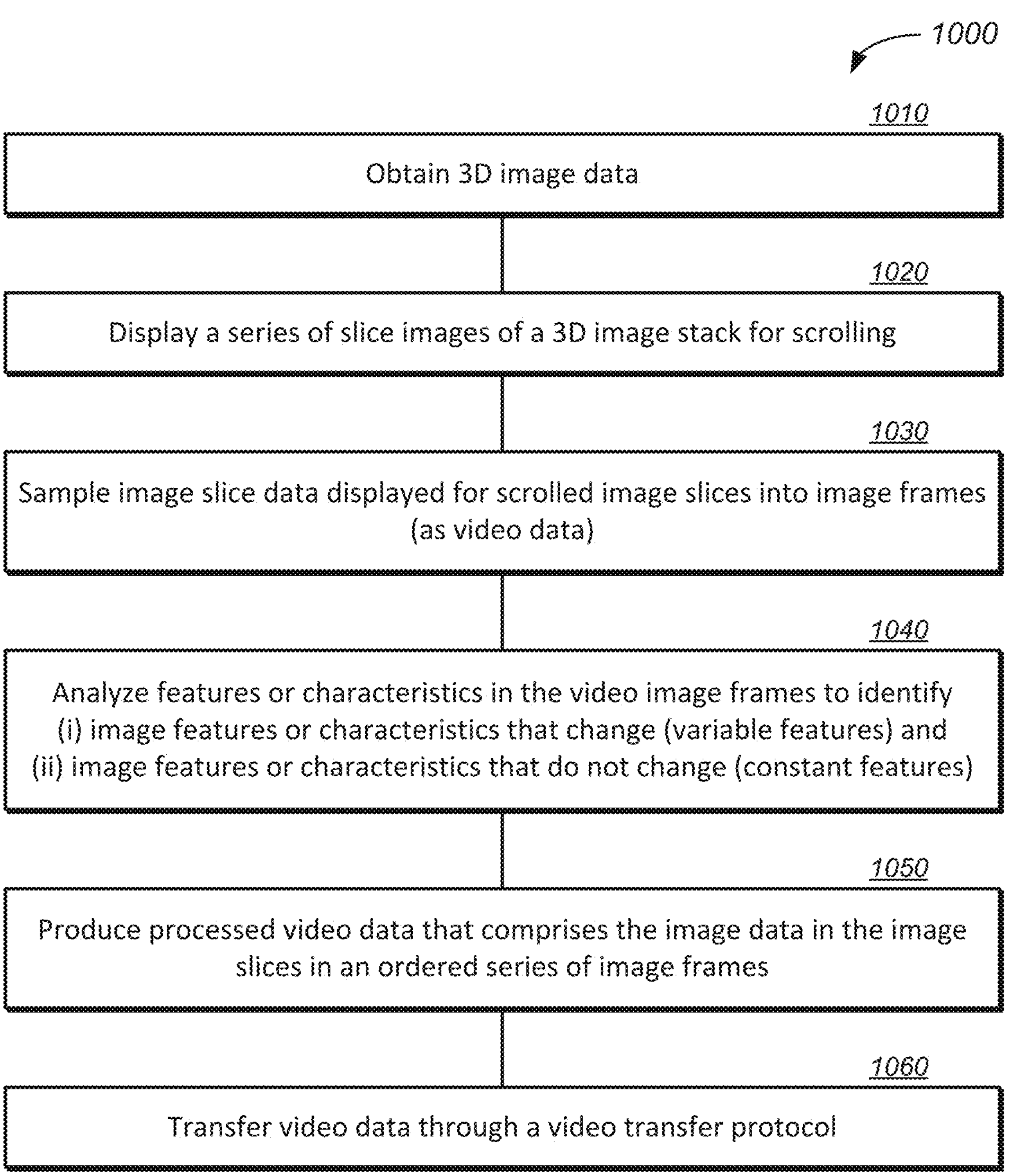
FIG. 1 is a flow diagram illustrating a method for providing real-time 3D image information from an imaging system to a medical device in accordance with various embodiments of the present technology.

The present disclosure is directed to systems, devices, methods and computer program products for providing 3D image data collected by an imaging system that is processed and transferred as video data to a medical device in real time. In some embodiments, for example, the disclosed techniques process 3D volumetric image data acquired by a Cone Beam CT (CBCT) system and reproduce it in a video data format for transfer to a medical device, e.g., a robotic diagnostic or surgical catheter device, in real time while the medical device is implemented in a medical procedure. In this manner, the medical device can utilize updated anatomical information from the 3D image data while the medical device is being operated inside the patient's body during the medical procedure. Implementations of the disclosed systems, devices, methods and computer program products provide an alternative way to transfer the 3D volume image data from an imaging system to a medical device that bypasses standard image data communication networks, e.g., such as the DICOM standard, which may be unreliable, if even available.

A computing system implementing the disclosed technique converts 3D image data from an imaging system to an accurate representation of the 3D image data in video data format and transfers the video data to the medical device for real-time usage. In implementations of the disclosed technique, a user or operator of the medical device (e.g., a physician) scrolls a stack of 3D images, which is displayed on a monitor in communication with the imaging system. Each image in the stack may feature a multi-planar reconstruction (MPR) visualization of the 3D volume data set showing standard axial, sagittal and coronal cross-sectional views. For example, an MPR visualization can be arranged as 2×2 windows displaying each 2D planar view and a volumetric view, where one view-axis (i.e., the scrolling view) changes as the user scrolls between image slices in the stack. The user can scroll the stack of images from the beginning to end of the stack, which displays all of the content in the 3D volume data set; or the user may scroll a subset of image slices, allowing conversion of partial volumetric data of interest. In some example implementations, the x-coordinate and y-coordinate would be constant values in each scrolled slice when the user scrolls the slices by varying the z-coordinate. In this manner, once the z-coordinates for each slice are recovered, the volume data can be reconstructed by resampling the slices so that the z values fall on a regular grid with a defined interval. As such, the scrolled stack of images are captured, processed to reproduce the data in a standard video data format (e.g., NTSC, HD or other), and transferred from the imaging system to the medical device system (that includes the medical device instrument) through a video transfer protocol (e.g., RTP, RTSP, RIST-type protocols, TCP-based protocols, UDP-based protocols, etc.) using various communication techniques or directly by video capture (e.g., via frame grabber card). The computing system implementing the disclosed technique analyzes captured information from each image slice in the stack to (i) recover the varying slice location (e.g., z-value variations) of each image slice and (ii) verify the non-varying slice information remains constant (e.g., x- and y-values remain constant).

Specific details associated with several embodiments of the present technology are described herein, some with reference to FIGS. 1-12. Although some of the embodiments are described with respect to particular medical systems and devices in the context of navigating and performing medical procedures within lungs of a patient, other applications and other medical system and medical device embodiments in addition to or alternative to those described herein are within the scope of the present technology. For example, unless otherwise specified or made clear from context, the devices, systems, methods, and computer program products of the present technology can be used for various image-guided medical procedures, such as medical procedures performed on, in, or adjacent hollow patient anatomy, and, more specifically, in procedures for surveying, biopsying, ablating, or otherwise treating tissue within and/or proximal the hollow patient anatomy. Thus, for example, the systems, devices, methods, and computer program products of the present disclosure can be used in one or more medical procedures associated with other patient anatomy, such as the bladder, urinary tract, and/or heart of a patient.

It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

As used herein, the term "physician" shall be understood to include any type of medical personnel who may be performing or assisting a medical procedure and, thus, is inclusive of a doctor, a nurse, a medical technician, other similar personnel, and any combination thereof. Additionally, or alternatively, as used herein, the term "medical procedure" shall be understood to include any manner and form of diagnosis, treatment, or both, inclusive of any preparation activities associated with such diagnosis, treatment, or both. Thus, for example, the term "medical procedure" shall be understood to be inclusive of any manner and form of movement or positioning of a medical device in an anatomical chamber. As used herein, the term "patient" should be considered to include human and/or non-human (e.g., animal) patients upon which a medical procedure is being performed.

A. Embodiments of Techniques for Converting and Transferring 3d Image Data to a Medical Device Presently, most sophisticated imaging systems like computerized tomography (CT), magnetic resonance imaging (MRI), ultrasonography, etc. utilize the DICOM standard, which specifies a non-proprietary data interchange protocol, digital image format, and file structure for medical images and image-related information. To transfer data using the DICOM standard, both equipment (e.g., the imaging system computer and the medical device system computer) are connected through a DICOM interface. Yet, in many clinical settings such as operating rooms, transferring image data and image-related information collected by an imaging system in real-time for use in a medical procedure can be unavailable, unreliable, or inadequate when utilizing DICOM. For example, some clinical settings lack the infrastructure to provide a DICOM network for image data transfer, while other clinical settings may suffer from network disablement or security issues that cause the established DICOM network from operating efficiently and consistently.

It would, therefore, be advantageous to utilize an alternative approach to provide volumetric image data in real-time for use in the medical procedure by a medical device that requires or would benefit from the volumetric image data obtained by the imaging system. Yet, to do so is significantly challenging. For example, the DICOM standard does not define a simple "plug and play" hardware and software specification that can be modified to work in another I/O port or by other protocols; rather, the DICOM standard defines a specific data form and flow for data transfer that convey images and related information between the computers. Any alternative approach to DICOM for real-time use of the 3D image data constitutes a wholesale change one that must preserve integrity of the data. If the format of the 3D image data is to be altered for transfer, then the image data must be converted or re-created accurately with respect to the original 3D volume data set acquired by the imaging system.

In the disclosed techniques, for example, the 3D volume data displayed on the display screen is converted to a video data file that accurately places each image in the stack in the right location along a varying axis (e.g., z-axis) and properly aligns the planar information of each slice image (e.g., x-y coordinate data). To do so, further challenges arise in verifying the image slices are placed in the correct order, where each image slice is organized by the location of its varying axis (e.g., z-value) in the proper sequence. For example, if a user was to scroll through the images on the display at a constant speed, then the organized conversion to video data format could occur by sampling at the matched constant speed. As a practical matter, however, this constant scrolling scenario does not occur, as the user will generally scroll partially through the stack, stop, back-up, continue, etc., or just not be able to scroll through every desired slice from beginning to end at a known, constant speed. What is needed is a reliable, effective and efficient process (e.g., non-taxing of computing resources) to provide the entire or partial volumetric data of interest from 3D image data to other devices during concurrent procedures, such as intra-operative medical imaging during a medical procedure with a medical device.

The disclosed systems, devices, methods and computer program products provide an algorithm to convert 3D image data from an imaging system to a format transferrable and processable by the medical device that captures user-desired image information and preserves the accuracy of the image data agnostic to the behavior of the user when scrolling through the image slices.

In some embodiments, a computer-implemented method includes sampling user-viewed slices of a 3D image stack, processing the sampled image data to accurately reproduce the data in video data format, and transferring the video data to the medical device. An example embodiment of such a method is described below in connection with FIG. 1.

FIG. 1, for example, is a flow diagram illustrating a method 1000 for providing real-time 3D image information from an imaging system to a medical device in accordance with various embodiments of the present technology. The method 1000 is illustrated as a set of operations or processes 1010-1060. All or a subset of the steps of the method 1000 can be implemented by a computing device, such as a control system in communication with or integrated with a medical system or device. Alternatively or in combination, all or a subset of the steps of the method 1000 can be implemented by a control system of a medical instrument system or device, including but not limited to various components or devices of a robotic or teleoperated system, as described in greater detail below. The computing system for implementing the method 1000 can include one or more processors operably coupled to a memory storing instructions that, when executed, cause the computing system to perform operations in accordance with some or all of the processes 1010-1060 of the method 1000.

Beginning at process 1010, the method 1000 obtains, at a computer in communication with a volumetric imaging system and a display monitor, 3D image data including volume data reconstruction images of an anatomical structure of a patient imaged using the imaging system. In some implementations, the computer in communication with the volumetric imaging system and the display monitor are part of a single imaging system, such as a CT, CBCT, Mill or other imaging system. In some implementations of the process 1010, an external display monitor (i.e., monitor external to the imaging system) receives the 3D image data as a stream from the volumetric imaging system, where the external display monitor can be a monitor in communication with a computer of a medical device system.

Figure 3A:
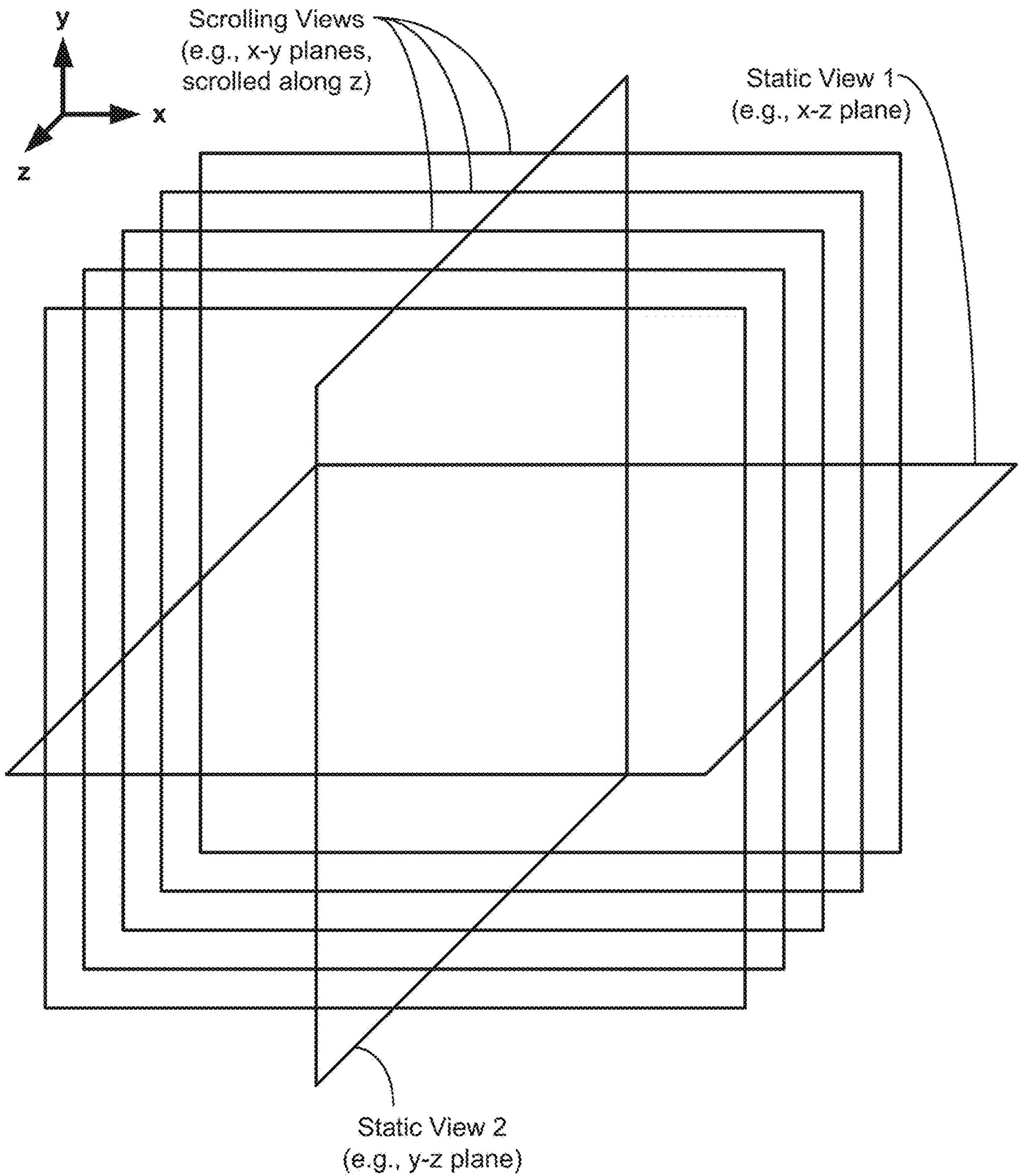
FIG. 3A is a diagram illustrating a stack of 3D images depicting two static views of two dimensional (2D) planes and scrolling views of image slices within one 2D plane.
Figure 3B:
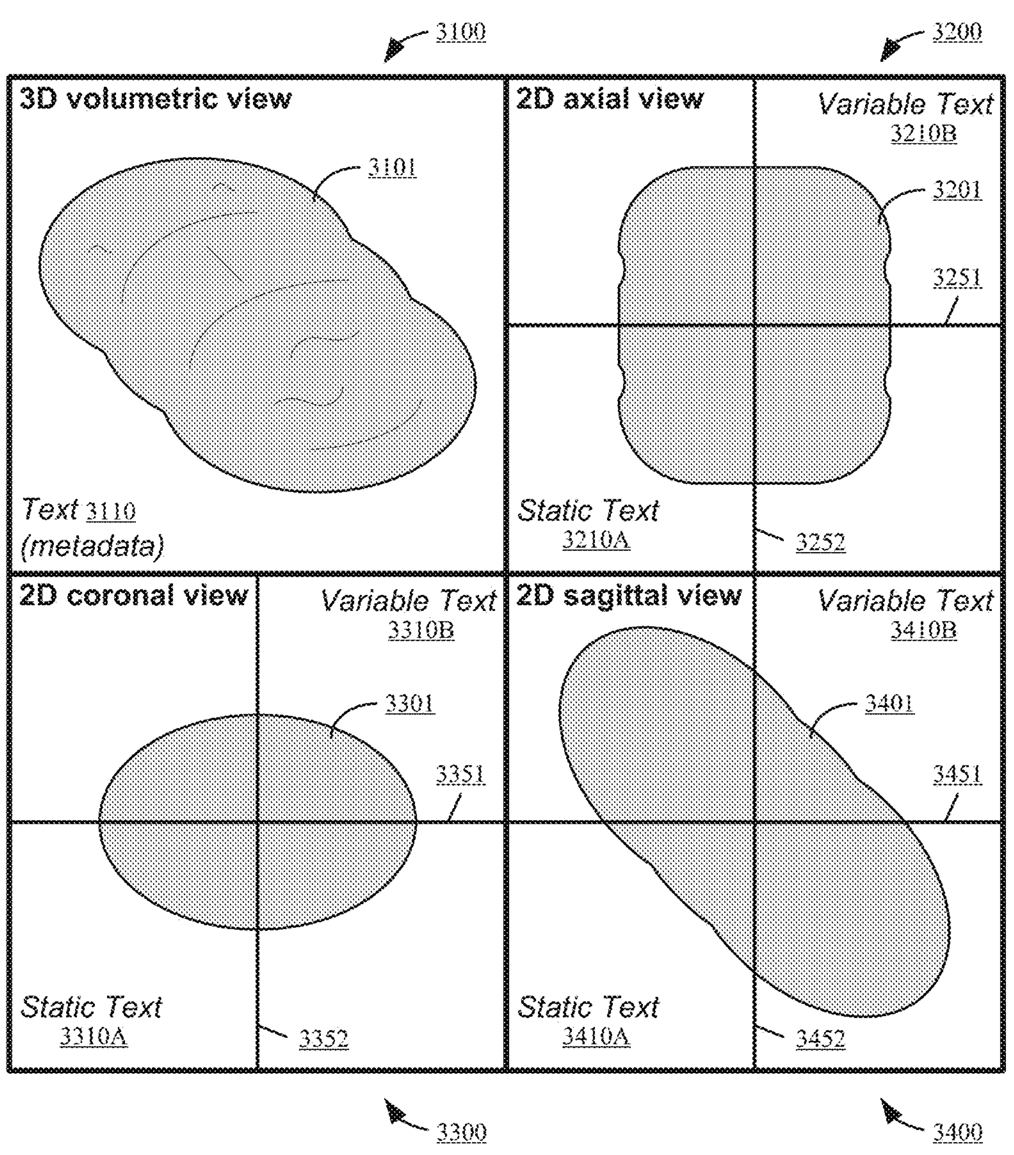
FIG. 3B is a diagram illustrating an image visualization window depicting 2D planar views and a volumetric view of an image slice from a stack of 3D images.

At process 1020, the method 1000 displays, on the display monitor, the volume data reconstruction images in a series of image slices of a scrolled stack, where each image slice includes at least one static view and one scrolling view that changes when a user scrolls between two images of the volume data reconstruction images. Examples of the 3D image data and volume data reconstruction images are shown in FIGS. 3A, 3B, and 4B and described in further detail below.

At process 1030, the method 1000 samples the data displayed on the display monitor for each displayed image slice into image frames as video data for a standard video data format (e.g., NTSC, HD or other). In various embodiments, a computing device that implements the process 1030 can be, for example, the computer of the volumetric imaging system that includes a computer program product in accordance with embodiments of the disclosed techniques for executing the sampling process. In other embodiments, a computing device that implements the process 1030 can be, for example, a computer of the control system of the medical instrument system or device, discussed in greater detail below in this disclosure. Other examples of computing devices that implements the process 1030 are discussed in further detail below.

The sampling process of the scrolled images can be implemented in various ways. In some implementations of the processes 1020-1030, for example, the user is prompted to start and to stop the sampling of the scrolled images that are displayed from the stack of image slices (of interest to the user). In some implementations of the processes 1020-1030, the sampling process is implemented based on a time period determined by changes in the sampled data, e.g., where the sampling is stopped after a predetermined time where no changes in the last sampled image slice is detected. In still further implementations of the process 1030, the sampling can include a screen capture technique.

At process 1040, the method 1000 analyzes the sampled data to detect one or more features or characteristics in the image frames and identify (i) features or characteristics in each scrolled image that change (variable features) and (ii) features or characteristics in each scrolled image that do not change (constant features).

At process 1050, the method 1000 continues with producing processed video data that comprises the image data in the image slices in an ordered series of image frames. For example, the ordered series of image frames can be organized in a slice sequence along the user-scrolled coordinate axis, e.g., where planar coordinates associated with the imaged anatomical structure remain constant for each image slice in the series of slice images in the scrolled stack.

In some embodiments of the processes 1040 and 1050 (described in connection with FIG. 2), text features in the sampled image data are detected to determine a constant text and a variable text in each scrolled image slice and identify a changing coordinate value overlaid on each image slice in the scrolled stack. Alternatively or additionally, in some embodiments of the processes 1040 and 1050 (described below in connection with FIG. 4A), static and scrolled views of the sampled image data (e.g., MPR visualization images) are identified by image features, and one or more image features that are within static views are detected to determine a location of the scrolling views for each image slice in the scrollable image stack. Alternatively or additionally, in some embodiments of the processes 1040 and 1050 (described below in connection with FIG. 5), partial regions of the sampled image slices are analyzed to index the images slices for creating a pseudo volume image data set.

At process 1060, the method 1000 transfers the video data through a video transfer protocol (e.g., RTP, RTSP, RIST-type protocols, TCP-based protocols, UDP-based protocols, etc.), which can be implemented by various communication processes including wired or wireless techniques. In some embodiments of the process 1060, the method 1000 transfers the video data directly by video capture (e.g., via frame grabber card). In some implementations, the process 1060 is implemented after the process 1030; whereas in other implementations, the process 1060 is implemented after the process 1040 or after the process 1050.

As an example, the process 1060 can be implemented after the process 1030 to transfer the video data of non-analyzed sampled image slice data to the computing device in communication with the medical device for implementation of the processes 1040 and 1050. Whereas, in other example implementations of the method 1000, the process 1060 can be implemented after either of the processes 1040 or 1050 to transfer partially- or fully-analyzed and/or produced video data that was processed by a computer program product in accordance with the disclosed technology executable on the computer of the imaging system, such that the partially- or fully-analyzed and/or produced video data is received at the computing device in communication with the medical device.

In some implementations of the method 1000 where the computing device is included in a robotic or teleoperated medical system, the computing device is in data communication with a medical device system, which includes a medical device having a sensor to generate position sensor data and/or motion sensor data when the medical device is driven in an anatomical structure or structures of the patient (e.g., driven through anatomic passageway(s) of the patient). The position sensor data is associated with one or more positions of the medical device within the anatomic passageway, and the motion sensor data is associated with the translational motion and/or the rotational motion of the medical device within the anatomic passageway(s). Optionally, in some embodiments, the medical device system includes an image capture device configured to capture image data of patient anatomy within the anatomic passageway. In this manner, the robotic or teleoperated medical system can implement the method 1000 as part of a medical procedure on the patient that utilizes the 3D image data imaged in real-time with the medical procedure that is processed and transferred as video data for use by the robotic or teleoperated medical system. An example of the robotic or teleoperated medical system is discussed in greater detail below in connection with FIGS. 6 and 7.

In some implementations of the method 1000, for example, the computing device of the robotic or teleoperated medical system can provide the processed video data to a point cloud processing module of the medical device to process the image frames and extract information used in a navigation data point cloud for the medical device (e.g., while navigating through the anatomical passageway(s) of the patient during the medical procedure). In some implementations, for example, the computing device of the robotic or teleoperated medical system can generate a point cloud of coordinate points based at least in part on the position sensor data and/or the motion sensor data, generate a registration between at least a portion of the point cloud and at least a portion of a pre-operative image of the anatomical region, extract data from the ordered set of image frames in the processed video data to produce coordinate points associated with the imaged anatomical region by the imaging system, and update the registration based at least in part on the produced coordinate points associated with the imaged anatomical region.

Although the steps of the method 1000 are discussed and illustrated in a particular order, a person of ordinary skill in the relevant art will recognize that the method 1000 can be altered and still remain within these and other embodiments of the present technology. In other embodiments, for example, the steps of the method 1000 can be performed in a different order. Additionally, one or more steps of the method 1000 illustrated in FIG. 1 can be omitted or consolidated. For example, the processes 1010, 1020 and/or 1030 can be implemented in one process. Furthermore, one or more steps of the method 1000 illustrated in FIG. 1 can be implemented differently in various implementations of the method 1000. For example, the processes 1030, 1040, 1050 and/or 1060 can be implemented in accordance with the methods 2000, 4000 or 5000 as described below. Optionally, one or more steps of the method 1000 can be repeated. For example, the processes 1040 and 1050, as implemented in accordance to the methods 2000 and 4000 described below, can be repeated in any sequence, e.g., which can be used to validate the other of methods 2000 or 4000.

1. Example Embodiments Using Text Feature Recognition

In some embodiments of the method 1000, after the computing device samples the scrolled images displayed on the imaging system monitor to video data (i.e., video image frames), the processes 1040 and 1050 can be implemented based on a text feature recognition technique, such as an optical character recognition (OCR) technique, to determine variable text in each scrolled image slice and identify a changing coordinate value overlaid on each image slice in the scrolled stack. For example, the displayed information from each image slice in the stack will depict (i) a varying slice location (e.g., z-value variations along the z-coordinate axis) of each image slice and (ii) non-varying or constant slice information (e.g., x- and y-values that remain constant along the x-coordinate and y-coordinate axes).

Typically, for 3D volumetric images such as MPR visualization images, there will be information in each data slice that will be constant, such as metadata. Example metadata that is displayed in MPR images can include, for example, the patient name or identification (ID), scanning parameters, imaging system information, etc. In some instances, the metadata includes the x-coordinate, the y-coordinate and the z-coordinate displayed in the MPR images, particularly in the scrollable view where two of the coordinates are constants across the scrolled stack as the other coordinate varies—an example being the z-coordinate changing in scrolling views of the x-y planes, where the x-coordinate and the y-coordinate remain constant, as shown in FIG. 3A and discussed in greater detail below. Since at least the metadata will be static (i.e., this information does not change with the action of scrolling), the computing device implements the OCR text detection technique to isolate the area where there is text overlay. The computing device implements a change detection technique on the isolated area (with the text overlay) to detect text that has changed between image slices. For example, OCR can be used to convert the coordinate from image pixels to a numerical value. The determined changing text (e.g., numerical z-value) is used to organize the image frame data in the proper sequence. The processed video data may optionally be screened (e.g., autonomously or based on user control) to verify that the sampled image slice data is organized according to sequential scrolling index (e.g., values of the scrolling axis, such as the numerical z-values), thereby providing a check on the reproduced video data to validate organizational accuracy.

Figure 2:
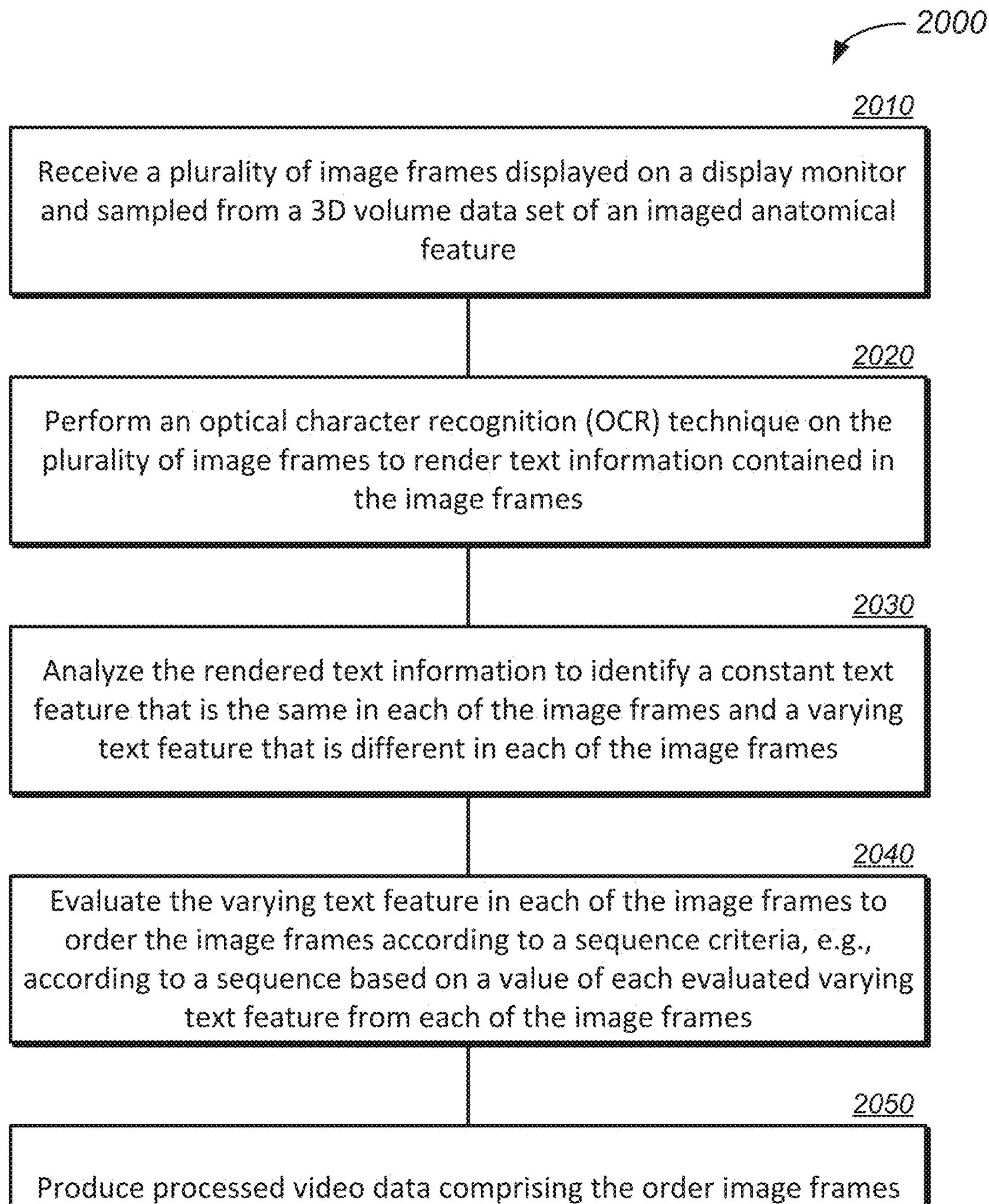
FIG. 2 is a flow diagram illustrating a flow diagram of an example of a method for analyzing text features of video image frames and producing processed video data in accordance with various embodiments of the method of FIG. 1.

FIG. 2, for example, is a flow diagram depicting an example of a method 2000 for analyzing text features of video image frames and producing processed video data in accordance with some embodiments of the method 1000. The method 2000 can be implemented, for example, at processes 1040 and 1050 in some embodiments of the method 1000. Alternatively or in combination, all or a subset of the steps of the method 2000 can be implemented by a control system of a medical instrument system or device, including but not limited to various components or devices of a robotic or teleoperated system, as described in greater detail below. The computing system for implementing the method 2000 can include one or more processors operably coupled to a memory storing instructions that, when executed, cause the computing system to perform operations in accordance with some or all of the processes 2010-2050 of the method 2000.

Beginning at process 2010, the method 2000 receives a plurality of image frames that were sampled from a 3D volume data set while being displayed as a series of slice images scrolled by a user. The plurality of sampled image frames correspond to the displayed image slices from the scrolled stack of images of an anatomical structure of a patient's anatomy imaged by an imaging system. In some implementations, for example, the sampled image frames received at the process 2010 correspond to a plurality of volume data reconstruction images that were displayed on a display monitor as the user scrolls through the series of slice images in the stack, e.g., at process 1030 of the method 1000.

At process 2020, the method 2000 performs an OCR technique on the plurality of image frames to render text information contained in the image frames. A variety of suitable OCR techniques may be used. At process 2030, the method 2000 analyzes the rendered text information to identify a constant text feature that is the same in each of the image frames and a varying text feature that is different in each of the image frames.

At process 2040, the method 2000 evaluates the varying text feature in each of the image frames to sort and order the image frames, e.g., according to a sequence criteria. In implementations of the process 2040, for example, the image frames are sorted and ordered according to an ascending or descending sequence based on a value of each evaluated varying text feature from each of the image frames. At process 2050, the method 2000 produces processed video data comprising the ordered image frames.

In some embodiments, the method 2000 may optionally include a process to allow the user to verify that the ordered set of the image frames is organized according to the series of image slices of the scrollable image stack by allowing the user to view the processed video data on a display screen and provide an input associated with a verification or non-verification of the processed video data. In some embodiments, the method 2000 may optionally include a process to autonomously verify the ordered set of the image frames in the processed video data.

FIG. 3A shows a diagram illustrating an example 3D volume data set depicted as a stack of 3D image slices in one 2D plane (scrolling views) and two that are intersected by two static views of 2D planes. In the example, the scrolling views are the x-y planes that are scrollable by the user along the z-axis, which are intersected by Static View 1 in the x-z plane and Static View 2 in the y-z plane. The example stack of 3D images can be presented to the user as MPR visualization images.

FIG. 3B shows an example of an MPR visualization depicting a 2×2 window of the three 2D planar views and a volumetric view of an image slice from a stack of 3D images. In the example MPR visualization diagram of FIG. 3B, four windows 3100, 3200, 3300, and 3400 are arranged in 2×2 window configuration. Window 3100 represents a three-dimensional volumetric view of an anatomical structure or region 3101 of a patient's anatomy imaged by the imaging system, e.g., CT, CBCT, MRI, etc. In window 3100, text 3110, such as metadata, appears in one or some portion of the image view.

Windows 3200, 3300 and 3400 represent two-dimensional image views of the anatomical structure or region 3101 at one slice in a series or stack of image slices. The window 3200, for example, is a 2D axial (or horizontal) view of the anatomical structure or region 3101, shown as 2D imaged anatomical feature 3201. In window 3200, there is text, such as metadata, that is displayed in portions of the 2D axial image view. More specifically, as shown in window 3200, static text 3210A is included in the 2D axial image view. Windows 3300 and 3400 showing the 2D coronal view of 2D imaged anatomical feature 3301 and 2D sagittal view of 2D imaged anatomical feature 3401, respectively, include static text features 3310A and 3410A, respectively, similar to static text feature 3210A shown in window 3200.

Typically, the MPR visualization allows the user to scroll one 2D view at a time, holding the other two 2D views constant at their two coordinates. In such instances, there will be variable text features along the scrolled 2D view for each image slice scrolled in that 2D view. For example, if the user scrolls the 2D coronal view, then variable text 3310B will also be included (along with static text 3310A) in the window 3300; and windows 3200 and 3400 may not include variable text. Likewise, for example, if the user scrolls the 2D axial view, then variable text 3210B will also be included (along with static text 3210A) in the window 3200; and windows 3300 and 3400 may not include variable text. Also, for example, if the user scrolls the 2D sagittal view, then variable text 3410B will also be included (along with static text 3410A) in the window 3400; and windows 3200 and 3300 may not include variable text.

Notably, as the user scrolls the 2D image slices of the stack, the static text 3210A, 3310A and 3410A do not change between image slices, whereas the variable text 3210B, 3310B or 3410B changes (i.e., variable text changes based on the scrolled view). It is noted that the location of the static text 3210A and variable text 3210B can be proximate or distant to each other, where the diagram of FIG. 3B depicts their respective locations for illustrative purposes only.

Typically, the text (e.g., metadata) in the 2D slice images includes coordinate information (e.g., in an x-, y-, z-coordinate system) regarding a location of each slice relative to other slices. The textual coordinates can be graphically represented, in each 2D view, by two slice lines perpendicular to each other. Window 3200, for example, includes slice line 3251 and slice line 3252 corresponding to two coordinate directions, e.g., x-direction to slice line 3251 and z-direction corresponds to slice line 3252 in this example. Similarly, window 3300 includes slice line 3351 and slice line 3352 corresponding to two coordinate directions, e.g., x-axis corresponds to slice line 3351 and y-axis corresponds to slice line 3352 in this example. Also, window 3400 includes slice line 3451 and slice line 3452 corresponding to two coordinate directions, e.g., z-axis corresponds to slice line 3451 and y-axis corresponds to slice line 3452 in this example.

The coordinates of the point that is the intersection of the three views can be denoted as $(x_i, y_i, z_i)$ for video frame i. Assuming the user is scrolling the image slices by varying the z-coordinate, then in this case the $x_i=x$ value is a constant, the $y_i=y$ value is a constant, and only the $z_i=z$ value changes. In order to reconstruct the volume data, $\{z_i\}$ needs to be recovered. Once $\{z_i\}$ is recovered, the volume can be reconstructed by resampling the slices so that the z values fall on a regular grid with a defined interval.

2. Example Embodiments Using Static View Image Feature Recognition

In some embodiments of the method 1000 (FIG. 1), after the computing device samples the image slices displayed on the imaging system monitor to video data (i.e., video image frames), the processes 1040 and 1050 can be implemented based on detecting and analyzing image features that are characteristic of static views in the standard MPR visualization. For example, the MPR visualization for each image slice typically displays image lines (e.g., slice lines) that should have the same value associated with the static views. In some examples, the slice line associated with a particular 2D plane are marked by the same color across the other views. By finding the slice lines that are identical or best matching in two views, two coordinates can be determined. Alternatively or additionally, the computing device can analyze the geometry of the lines, e.g., which can be advantageous in case the MPR display program does not use common colors between views. Notably, other image features (e.g., besides the slice lines) can be adapted for the matching process.

In some implementations, the computing device can analyze just one static view to identify the image feature(s) (e.g., slice line) in the one static view and determine its location in the associated scrolling view image. Whereas, in some implementations, the computing device can analyze two static views (in the 2×2 window of the MPR visualization images) to identify the image feature(s) (e.g., lines) in both of the static views and determine their location in the associated scrolling view image. For example, this can be implemented by matching two image features (e.g., slice lines) from the static view(s) to the corresponding line (e.g., corresponding by color detected by the algorithm) in the scrolling view to solve for the x-, y- and z-coordinates in each scrolled slice. The determined z-value is used to organize the image frame data to ensure the video data includes the sampled image frames in the proper sequence. The processed video data may optionally be screened (e.g., autonomously or based on user control) to verify that the sampled image slice data is organized according to sequential scrolling index (e.g., along the scrolling axis), thereby providing a check on the reproduced video data to validate organizational accuracy.

Figure 4A:
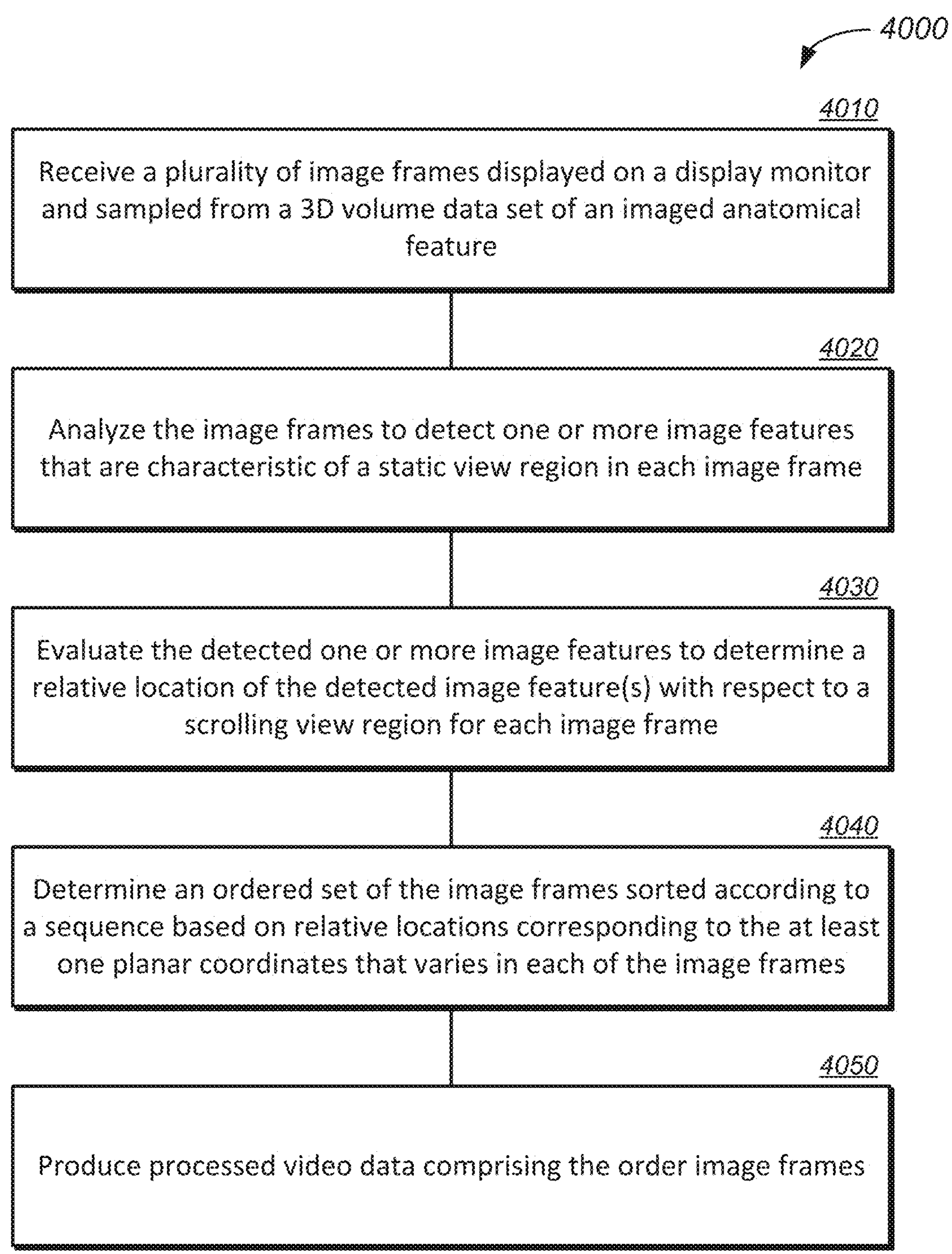
FIG. 4A is a flow diagram illustrating a method for analyzing image features of video image frames and producing processed video data in accordance with some embodiments of the method in FIG. 1.
Figure 4B:
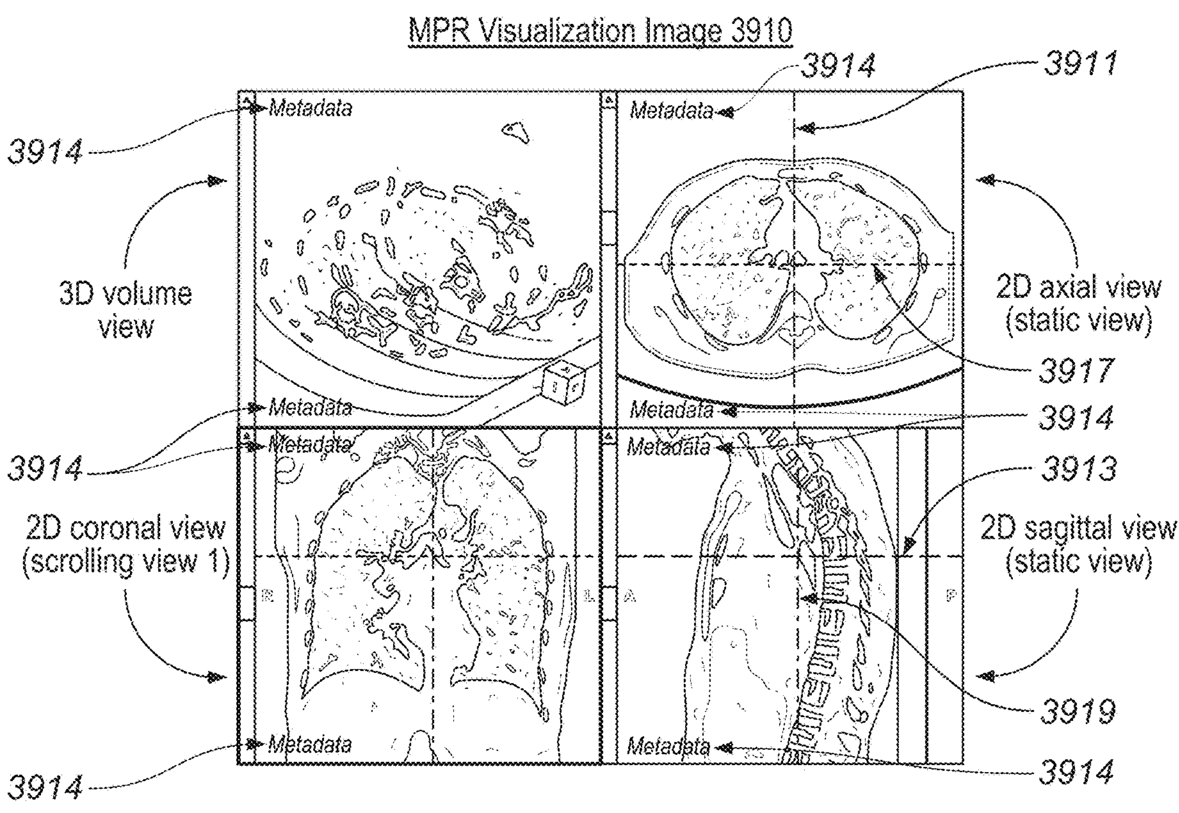
FIG. 4B is example visualization images of an imaged anatomical region of a patient's body where a scrolling view has changed from a first visualization image to a second visualization image.
Figure 4B:
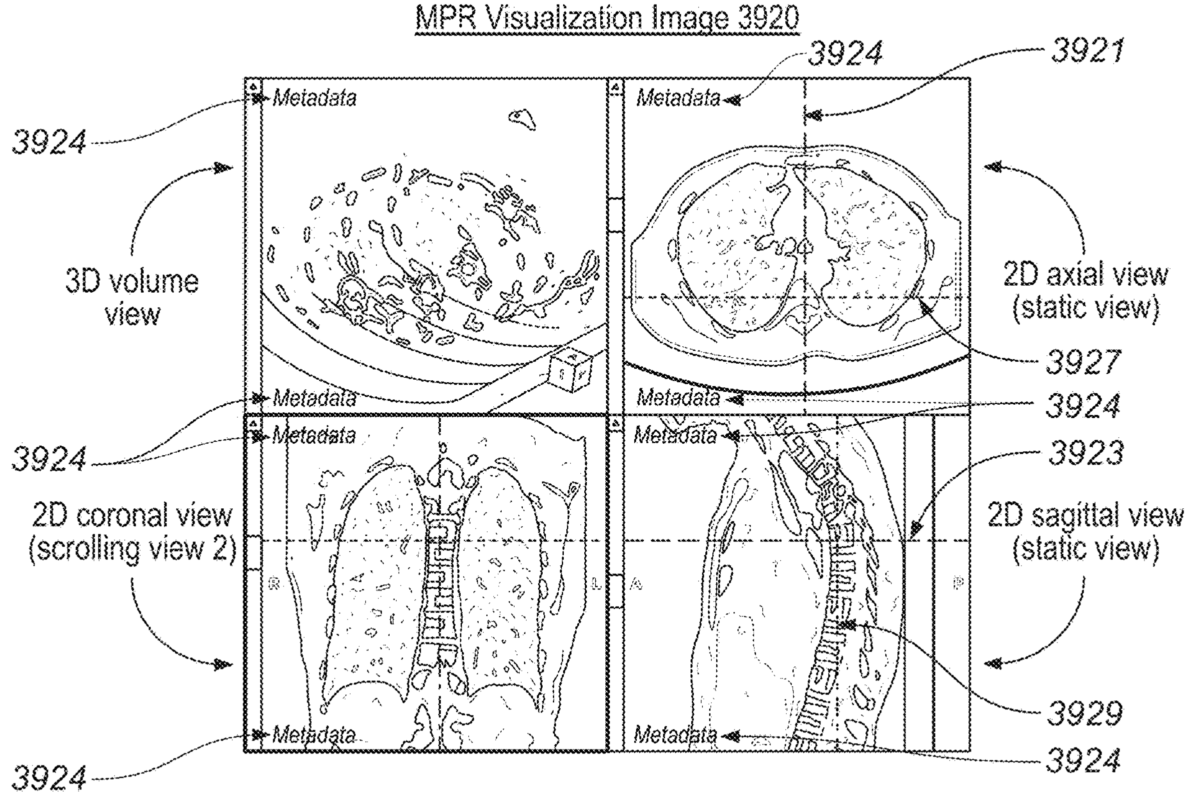

FIG. 4A, for example, is a flow diagram depicting an example of a method 4000 for analyzing image features of video image frames and producing processed video data in accordance with some embodiments of the method 1000 of FIG. 1. The method 4000 can be implemented, for example, at processes 1040 and 1050 in some embodiments of the method 1000. Alternatively or in combination, all or a subset of the steps of the method 4000 can be implemented by a control system of a medical instrument system or device, including but not limited to various components or devices of a robotic or teleoperated system, as described in greater detail below. The computing system for implementing the method 4000 can include one or more processors operably coupled to a memory storing instructions that, when executed, cause the computing system to perform operations in accordance with some or all of the processes 4010-4050 of the method 4000.

Beginning at process 4010, the method 4000 receives a plurality of image frames that were sampled from a 3D volume data set while being displayed as a series of slice images scrolled by a user. The plurality of sampled image frames correspond to the displayed image slices from the scrolled stack of images of an anatomical structure of a patient's anatomy imaged by an imaging system. In some implementations, for example, the sampled image frames received at the process 4010 correspond to a plurality of volume data reconstruction images that were displayed on a display monitor as the user scrolls through the series of slice images in the stack, e.g., at process 1030 of the method 1000 of FIG. 1.

The method 4000 continues at process 4020 with analyzing the plurality of image frames to detect one or more image features that are characteristic of a static view region in each image frame where planar coordinates (e.g., at or along one or more of a x-y plane, y-z, plane, or x-z plane) associated with the imaged anatomical region remain constant for each image slice in the series of image slices of the scrollable image stack. The planar coordinates that remain constant can include, for example, a point or a line along any one or a plurality of an x-y plane, y-z, plane, and/or x-z plane. Notably, in implementations of the process 4020, actual values for the planar coordinates associated with the detected image feature(s) that remains constant in the static view region do not need to be determined. In some implementations of the process 4020, to detect the one or more image features characteristic of a static view region, the computing device can compare different image grains to figure out what pixel(s) (of each image slice canvas) have changed and what pixel(s) remain static among each of the sampled image slices.

In one implementation, for example, the process 4020 can interrogate the sampled image slices and detect the slice lines in the 2D views of the example MPR visualization window. In the static views, one of the two intersecting slice lines remains constant for each static view in all of the sampled image slices in the image stack, i.e., the constant slice line has the same planar coordinate values for each image slice in that respective static view throughout the stack of image slices.

FIG. 4B shows example MPR visualization images of an imaged anatomical region of a patient's body (e.g., a chest CT volume data set) depicting two sets of 2×2 windows where the scrolling view has changed from a first MPR visualization image (MPR image 3910) to a second MPR visualization image (MPR image 3920). The 2D planar views (i.e., the 2D axial view, the 2D sagittal view, and the 2D coronal view) include two static views and one scrolling view. In this example, the two static views are the 2D axial view ("Static view 1") and the 2D sagittal view ("Static view 2"); and the scrolling view is the 2D coronal view ("Scrolling view" 1 . . . n, where n represents the number of image slices in the stack of images from the 3D data set along that scrolling view axis).

As shown in FIG. 4B, each MPR visualization image includes two lines that intersect for each of the 2D views. Some of these lines remain constant in relative position in each image slice for the corresponding 2D view in the image stack, while some of these lines vary in position in each image slice for the corresponding 2D view in the image stack. Constant lines are shown in the example of FIG. 4B as slice lines 3911 and 3913 in MPR image 3910 and as slice lines 3921 and 3923 in MPR image 3920—these lines do not change within the 2D axial view and 2D sagittal view, respectively, between MPR image 3910 and MPR image 3920. Varying lines are also shown in the example of FIG. 4B as slice lines 3917 and 3919 in MPR image 3910 and as slice lines 3927 and 3929 in MPR image 3920—these lines do change in their relative positions within the 2D axial view and 2D sagittal view, respectively, between MPR image 3910 and MPR image 3920. Each MPR visualization image can include other features or text such as, for example, metadata, labeled in the MPR image 3910 as 3914 and in MPR image 3910 as 3924.

As an example, referring to process 4020 in FIG. 4A and the diagram of FIG. 4B, in the 2D axial views (static view) for MPR Visualization Images 3910 and 3920, the vertical slice line 3911 in MPR image 3910 is constant (i.e., same relative position with respect to the image window) in its location with respect to vertical slice line 3921 in MPR image 3920. In this manner, the process 4020 can determine the unchanged position of the slice line in the static views of the stack of images. In some examples, implementation of the process 4020 can interrogate the sampled image slices and detect other features pertaining to the slice line, such as whether lines share the same color across the other static views of the image slices in the stack. By finding the slice lines that are identical or best matching in two views, two coordinates can be determined.

At process 4030, the method 4000 evaluates the detected one or more image features to determine a relative location of the one or more image features in a scrolling view region for each image frame. In this manner, the process 4030 can determine where at least one of the planar coordinates associated with the imaged anatomical region varies for each image slice of the scrollable image stack.

In some implementations, for example, the process 4030 can examine the varying slice lines in the 2D views of the example MPR visualization window and determine the change in their position with respect to the image view, such that their varying relative location is indicative of the planar coordinates of the scrolling view in each image slice of the stack. As an example, referring again to FIG. 4B, in the 2D axial views (static view) for MPR Visualization Images 3910 and 3920, the horizontal slice line 3917 in MPR image 3910 varies in its location with respect to horizontal slice line 3927 in MPR image 3920; similarly, in the 2D sagittal views (static view) for MPR Visualization Images 3910 and 3920, the vertical slice line 3919 in MPR image 3910 varies in its location with respect to vertical slice line 3929 in MPR image 3920. In this manner, the process 4030 can determine, from the relative position changes of the slice lines between the static views, the relative position of the scrolling view in each image slice of the stack of images. This can be implemented, for example, using a single, varying slice line (e.g., horizontal slice line 3917 in 2D axial view of MPR image 3910 and horizontal slice line 3927 in 2D axial view of MPR image 3920) or using both varying slice lines (e.g., vertical slice line 3919 in 2D sagittal view of MPR image 3910 and vertical slice line 3929 in 2D sagittal view of MPR image 3920).

At process 4040, the method 4000 determines an ordered set of the image frames sorted according to a sequence based on relative locations corresponding to the at least one planar coordinates that varies in each of the image frames. In implementations of the process 4040, for example, the image frames are sorted and ordered according to an ascending or descending sequence based on a value prescribed to the varying feature detected to correspond to the order of scrolling views among the sampled image slices in the image stack. At process 4050, the method 4000 produces processed video data comprising the ordered image frames.

In some embodiments, the method 4000 optionally includes a process to allow the user to verify that the ordered set of the image frames is organized according to the series of image slices of the scrollable image stack by allowing the user to view the processed video data on a display screen and provide an input associated with a verification or non-verification of the processed video data. In some embodiments, the method 4000 optionally includes a process to autonomously verify the ordered set of the image frames in the processed video data.

The method 4000 may also optionally include a process to allow the user to verify the static views and/or the scrolling view in the volume data reconstruction images. In some embodiments, for example, a user may be prompted to input the static view and/or scrolling view or respond to a verification prompt, e.g. after implementation of the process 4030.

In some embodiments, the computing device implements the processes 1040 and 1050 of the method 1000 by implementing both the method 2000 and the method 4000, e.g., concurrently and/or sequentially. In this manner, the computing device can compare the determined order of the scrolling view image slices between the techniques. If any significant differences in the determined order exist (e.g., scrolling view coordinate values), the user can be prompted to further verify (and/or input) information pertaining to the order of images in the produced video data. In one example, the method 1000 may produce a pop-up window prompting the user to confirm the produced video of the user-scrolled 3D image slices are acceptable. In some examples, the method 1000 may produce a graphic user interface (GUI) that allows the user to re-sort the image frames.

Referring to the method 4000 in FIG. 4A, for example, after the process 4040 to determine the ordered set of the image frames, the method 4000 can optionally include a process to validate the ordered set of the image frames by re-analyzing the plurality of image frames based on a text-recognition technique, and a process to compare the ordered set of the image frames to the second ordered set of the image frames. In some implementations, for example, the optional process to validate the ordered set of the image frames in the method 4000 can include implementing processes 2020, 2030 and 2040, e.g., performing an OCR technique on the plurality of image frames to render text information contained in the image frames, analyzing the rendered text information to identify a constant text feature that is the same in each of the image frames and a varying text feature that is different in each of the image frames, and evaluating the varying text feature in each of the image frames to create a second ordered set of the image frames is sorted according to a sequence based on a value of each evaluated varying text feature.

3. Example Embodiments Creating Pseudo Volume Image Data

In some embodiments of the method 1000 (FIG. 1), after implementation of the processes 1010 and 1020 where the 3D image data is obtained by a computer in communication with a display monitor (e.g., the computer of the imaging system or the computing device in communication with the medical device) and the 3D image data is displayed on the monitor in a series of image slices of a 3D image stack for the user to scroll, the method 1000 can implement a modified sampling process to create a 'pseudo volume' in a video file format by stacking sampled image views from scrolled MPR visualization images from the original 3D image data. For example, image data from the 2D image views (e.g., axial, coronal, and sagittal views) can be at least partially sampled, analyzed for a change in image features or characteristics (e.g., pixel changes), and indexed when a change is determined so that the pseudo 3D volume is constructed by stacking the sampled image data according to the indexed sample image slice.

Figure 5:
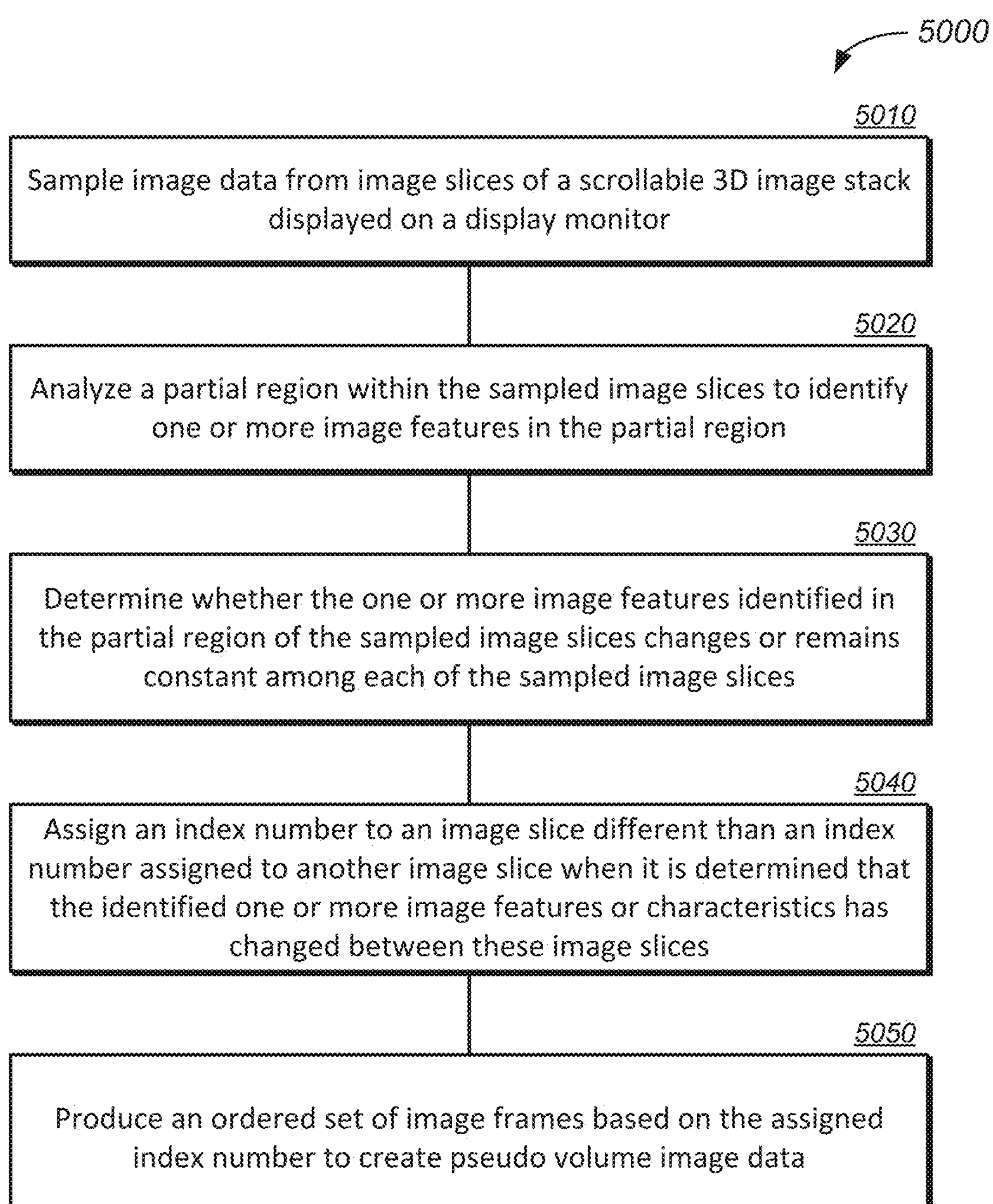
FIG. 5 is a flow diagram illustrating a method for analyzing displayed 3D volume image data and producing video data creating a pseudo volume of the 3D volume image data in accordance with some embodiments of the method in FIG. 1.

FIG. 5, for example, is a flow diagram depicting an example of a method 5000 for analyzing displayed 3D volume image data and producing video data creating a pseudo volume of the 3D volume image data in accordance with some embodiments of the method 1000. The method 5000 can be implemented after process 1010 or 1020 in some embodiments of the method 1000 of FIG. 1. Alternatively or in combination, all or a subset of the steps of the method 5000 can be implemented by a control system of a medical instrument system or device, including but not limited to various components or devices of a robotic or teleoperated system, as described in greater detail below. The computing system for implementing the method 5000 can include one or more processors operably coupled to a memory storing instructions that, when executed, cause the computing system to perform operations in accordance with some or all of the processes 5010-5050 of the method 5000.

Beginning at process 5010, the method 5000 samples image data from image slices of a 3D image stack of an imaged anatomical region of a patient that are displayed on a display monitor scrollable by the user. For example, the sampling produces a plurality of image frames from a 3D image stack (e.g., volume image data set) of the imaged anatomical region displayable on the display monitor. The sampling of the image data can be continuously performed, or such sampling can be performed based on an input, such as a user scrolling between slices. In various implementations of the process 5010, for example, the sampling can include a screen capture technique.

At process 5020, the method 5000 analyzes a partial region within the sampled image slices scrolled by the user to identify one or more image features or characteristics in the partial region.

At process 5030, the method 5000 determines whether the one or more image features or characteristics identified in the partial region of the sampled image slices changes or remains constant among each of the sampled image slices.

At process 5040, the method 5000 assigns an index number to a subsequent image slice different than an index number assigned to a previous image slice when it is determined that the identified one or more image features or characteristics has changed between the subsequent and the previous image slices. For example, implementation of the process 5040 can assign an index number to a first image frame of the sampled image frames that is different than an index number assigned to a second image frame of the sampled image frames when it is determined that the identified one or more image features or characteristics has changed between the first image frame and the second image frame. In implementations of the method 5000, for example, the process 5040 (or the process 5050) can delete or disregard sampled image frames where the identified one or more image features or characteristics between analyzed image slices is determined to remain constant.

At process 5050, the method 5000 produces an ordered set of image frames based on the assigned index number to create the pseudo volume image data. For example, the pseudo volume image data can include the information displayed on the monitor that was scrolled by the user.

Figure 6:
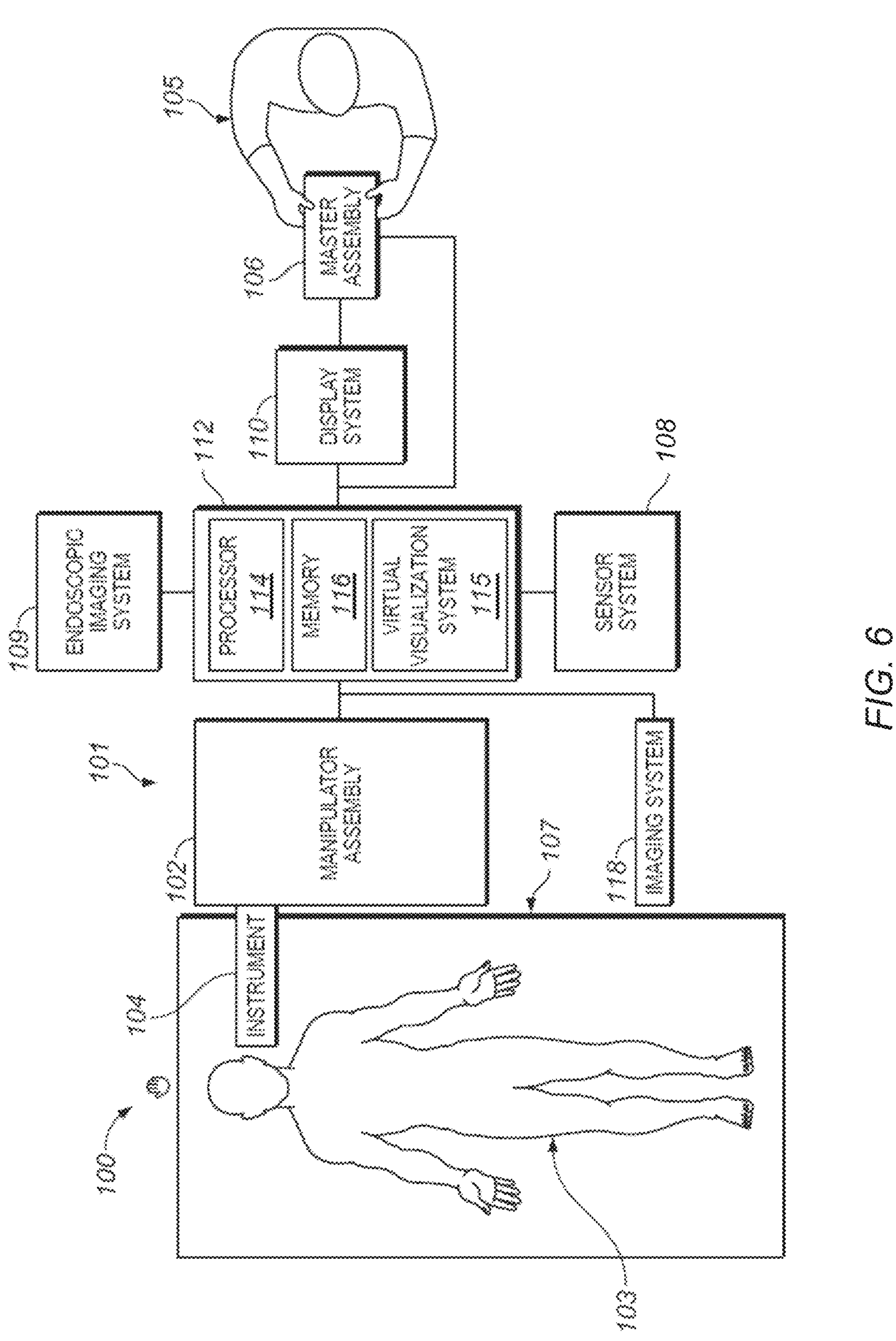
FIG. 6 is a schematic diagram of a robotic or teleoperated medical system configured in accordance with various embodiments of the present technology.

B. Embodiments of Robotic or Teleoperated Medical Systems for Implementing a Medical Procedure using Video Data Processed From the Imaging System FIG. 6 is a schematic representation of a robotic or teleoperated medical system 100 ("medical system 100") configured in accordance with various embodiments of the disclosed technology. The medical system 100 includes a medical device in communication with a computing device operable to implement the method 1000, 2000, 4000 and/or 5000, as disclosed above, to provide the medical system 100 with 3D image data of a patient obtained by another imaging system (e.g., CT, MRI, etc.) for real-time use during a medical procedure on the patient by the medical system 100.

As shown in FIG. 6, the medical system 100 includes a manipulator assembly 102, a medical instrument system 104, a master assembly 106, and a control system 112. The manipulator assembly 102 supports the medical instrument system 104 and drives the medical instrument system 104 at the direction of the master assembly 106 and/or the control system 112 to perform various medical procedures on a patient 103 positioned on a table 107 in a surgical environment 101. In this regard, the master assembly 106 generally includes one or more control devices that can be operated by an operator 105 (e.g., which can be a physician) to control the manipulator assembly 102. Additionally, or alternatively, the control system 112 includes a computer processor 114 and at least one memory 116 for effecting control between the medical instrument system 104, the master assembly 106, and/or other components of the medical system 100. The control system 112 can also include programmed instructions (e.g., a non-transitory computer-readable medium storing the instructions) to implement any one or more of the methods described herein, including instructions for providing information to a display system 110 and/or processing data for registration of the medical instrument 104 for various medical procedures on the patient by the medical system 100. The manipulator assembly 102 can be a teleoperated, a non-teleoperated, or a hybrid teleoperated and non-teleoperated assembly. Thus, all or a portion of the master assembly 106 and/or all or a portion of the control system 112 can be positioned inside or outside of the surgical environment 101.

In some embodiments, to aid the operator 105 in controlling the manipulator assembly 102 and the medical instrument system 104, the medical system 100 may further include one or more of the following: a sensor system 108, an endoscopic imaging system 109, an imaging system 118, a virtual visualization system 115, and/or the display system 110. In some embodiments, the sensor system 108 includes a position/location sensor system (e.g., an electromagnetic (EM) sensor system) and/or a shape sensor system for determining position, orientation, speed, velocity, pose, and/or shape of the medical instrument system 104 (e.g., while the medical instrument system 104 is within the patient 103). In these and other embodiments, the endoscopic imaging system 109 includes one or more image capture devices (not shown) (e.g., such as an imaging scope assembly and/or an imaging instrument) that records endoscopic image data, including concurrent or real-time images (e.g., video, still images, etc.) of patient anatomy. Images captured by the endoscopic imaging system 109 may be, for example, two or three-dimensional images of patient anatomy captured by an imaging instrument positioned within the patient 103, and are referred to hereinafter as "real navigational images."

In some embodiments, the medical instrument system 104 may include components of the sensor system 108 and/or of the endoscopic imaging system 109. For example, components of the sensor system 108 and/or components of the endoscopic imaging system 109 can be integrally or removably coupled to the medical instrument system 104. Additionally, or alternatively, the endoscopic imaging system 109 can include a separate endoscope (not shown) attached to a separate manipulator assembly (not shown) that can be used in conjunction with the medical instrument system 104 to image patient anatomy. The sensor system 108 and/or the endoscopic imaging system 109 may be implemented as hardware, firmware, software, or a combination thereof that interact with or are otherwise executed by one or more computer processors, such as the computer processor(s) 114 of the control system 112.

The imaging system 118 may be arranged in the surgical environment 101 near the patient 103 to obtain real-time and/or near real-time images of the patient 103 before, during, and/or after a medical procedure. In some embodiments, the imaging system 118 is included as part of the medical system 100. Whereas, as discussed above, in some embodiments, the imaging system 118 may be a separate system unaffiliated with the medical system 100. In some embodiments, the imaging system 118 includes a mobile C-arm cone-beam computerized tomography (CT) imaging system for generating three-dimensional images. For example, the imaging system 118 can include a DynaCT imaging system from Siemens Corporation or another suitable imaging system. In these and other embodiments, the imaging system 118 can include other imaging technologies, including MRI, fluoroscopy, thermography, ultrasound, optical coherence tomography (OCT), thermal imaging, impedance imaging, laser imaging, nanotube X-ray imaging, and/or the like. The images obtained by the imaging system 118 may be provided to the control system 112 of the medical system 118 by at least some of the processes described in accordance with the methods 1000, 2000, 4000 and/or 5000.

In these and other embodiments, the control system 112 further includes the virtual visualization system 115 to provide navigation assistance to the operator 105 when controlling the medical instrument system 104 during an image-guided medical procedure. For example, virtual navigation using the virtual visualization system 115 can be based upon reference to an acquired pre-operative or intra-operative dataset (e.g., based upon reference to data generated by the sensor system 108, the endoscopic imaging system 109, and/or the imaging system 118) of anatomic passageways of the patient 103. In some implementations, for example, the virtual visualization system 115 processes image data of the patient anatomy captured using the imaging system 118 (e.g., to generate an anatomic model of an anatomic region of the patient 103). The virtual visualization system 115 can register the image data and/or the anatomic model to data generated by the sensor system 108 and/or to data generated by the endoscopic imaging system 109 to (i) determine position, pose, orientation, shape, and/or movement of the medical instrument system 104 within the anatomic model (e.g., to generate a composite virtual navigational image), and/or (ii) determine a virtual image (not shown) of patient anatomy from a viewpoint of the medical instrument system 104 within the patient 103. For example, the virtual visualization system 115 can register the anatomic model to positional sensor data generated by the positional sensor system 108 and/or to endoscopic image data generated by the endoscopic imaging system 109 to (i) map the tracked position, orientation, pose, shape, and/or movement of the medical instrument system 104 within the anatomic region to a correct position within the anatomic model, and/or (ii) determine a virtual navigational image of virtual patient anatomy of the anatomic region from a viewpoint of the medical instrument system 104 at a location within the anatomic model corresponding to a location of the medical instrument system 104 within the patient 103.

The display system 110 can display various images or representations of patient anatomy and/or of the medical instrument system 104 that are generated by the sensor system 108, by the endoscopic imaging system 109, by the imaging system 118, and/or by the virtual visualization system 115. In some embodiments, the display system 110 and/or the master assembly 106 may be oriented so the operator 105 can control the manipulator assembly 102, the medical instrument system 104, the master assembly 106, and/or the control system 112 with the perception of telepresence.

As discussed above, the manipulator assembly 102 drives the medical instrument system 104 at the direction of the master assembly 106 and/or the control system 112. In this regard, the manipulator assembly 102 can include select degrees of freedom of motion that may be motorized and/or teleoperated and select degrees of freedom of motion that may be non-motorized and/or non-teleoperated. For example, the manipulator assembly 102 can include a plurality of actuators or motors (not shown) that drive inputs on the medical instrument system 104 in response to commands from the control system 112. The actuators can include drive systems (not shown) that, when coupled to the medical instrument system 104, can advance the medical instrument system 104 into a naturally or surgically created anatomic orifice. Other drive systems may move a distal portion (not shown) of the medical instrument system 104 in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the actuators can be used to actuate an articulable end effector of the medical instrument system 104 (e.g., for grasping tissue in the jaws of a biopsy device and/or the like).

Figure 7:
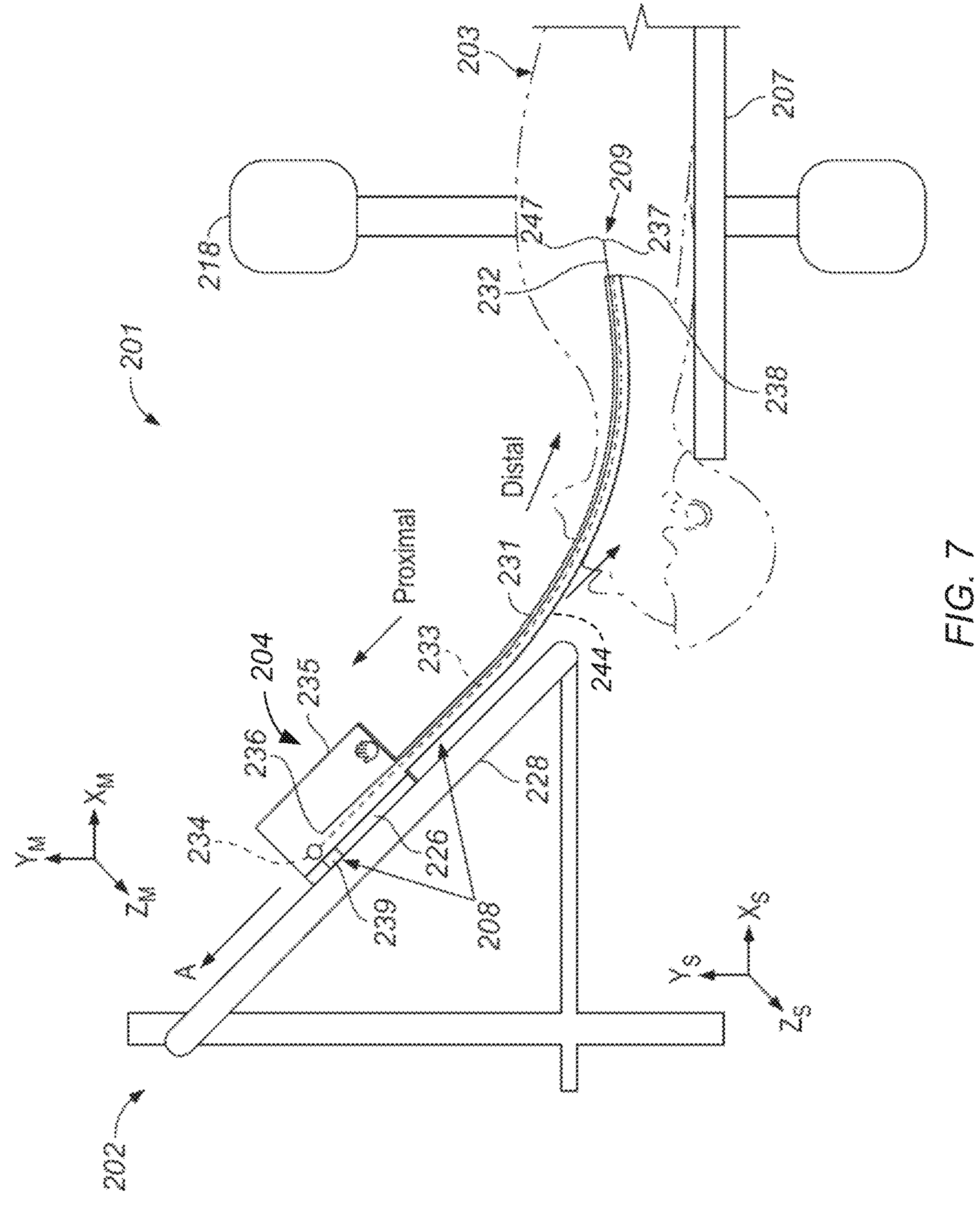
FIG. 7 is a schematic diagram of a manipulator assembly, a medical instrument system, and an imaging system configured in accordance with various embodiments of the present technology.

FIG. 7 is a schematic representation of a manipulator assembly 202, a medical instrument system 204, and an imaging system 218 in a surgical environment 201 and configured in accordance with various embodiments of the disclosed technology. In some embodiments, the manipulator assembly 202, the medical instrument system 204, and/or the imaging system 218 are the manipulator assembly 102, the medical instrument system 104, and/or the imaging system 118, respectively, of FIG. 6. As shown, the surgical environment 201 illustrated in FIG. 7 has a surgical frame of reference ($X_S$, $Y_X$, $Z_S$) in which a patient 203 is positioned on a table 207, and the medical instrument system 204 illustrated in FIG. 7 has a medical instrument frame of reference ($X_M$, $Y_M$, $Z_M$) within the surgical environment 201. During the medical procedure, the patient 203 may be stationary within the surgical environment 201 in the sense that gross patient movement can be limited by sedation, restraint, and/or other means. In these and other embodiments, cyclic anatomic motion of the patient 203, including respiration and cardiac motion, may continue unless the patient 203 is asked to hold his or her breath to temporarily suspend respiratory motion.

The manipulator assembly 202 includes an instrument carriage 226 mounted to an insertion stage 228. In some embodiments, the insertion stage 228 is fixed within the surgical environment 201. Alternatively, the insertion stage 228 can be movable within the surgical environment 201 but have a known location (e.g., via a tracking sensor or other tracking device) within the surgical environment 201. In these alternatives, the medical instrument frame of reference ($X_M$, $Y_M$, $Z_M$) is fixed or otherwise known relative to the surgical frame of reference ($X_S$, $Y_S$, $Z_S$). In the illustrated embodiment, the insertion stage 228 is linear, while in other embodiments, the insertion stage 228 is curved or has a combination of curved and linear sections.

The medical instrument system 204 of FIG. 7 includes an elongate device 231, a medical instrument 232, an instrument body 235, a sensor system 208, and an endoscopic imaging system 209. In some embodiments, the elongate device 231 is a flexible catheter that defines a channel or lumen 244. The channel 244 can be sized and shaped to receive the medical instrument 232 (e.g., via a proximal end 236 and/or an instrument port (not shown) of the elongate device 231) and facilitate delivery of the medical instrument 232 to a distal portion 238 of the elongate device 231. As shown, the elongate device 231 is coupled to the instrument body 235, which in turn is coupled and fixed relative to the instrument carriage 226 of the manipulator assembly 202.

In operation, for example, the manipulator assembly 202 can control insertion motion (e.g., proximal and/or distal motion along an axis A) of the elongate device 231 into the patient 203 via a natural or surgically created anatomic orifice of the patient 203 to facilitate navigation of the elongate device 231 through anatomic passageways of the patient 203 and/or to facilitate delivery of the distal portion 238 of the elongate device 231 to a target location within the patient 203. For example, the instrument carriage 226 and/or the insertion stage 228 may include actuators (not shown), such as servomotors, that facilitate control over motion of the instrument carriage 226 along the insertion stage 228. Additionally, or alternatively, the manipulator assembly 202 in some embodiments can control motion of the distal portion 238 of the elongate device 231 in multiple directions, including yaw, pitch, and roll rotational directions (e.g., to navigate patient anatomy). To this end, the elongate device 231 may house or include cables, linkages, and/or other steering controls (not shown) that the manipulator assembly 202 can use to controllably bend the distal portion 238 of the elongate device 231. For example, the elongate device 231 can house at least four cables that can be used by the manipulator assembly 202 to provide (i) independent "up-down" steering to control a pitch of the distal portion 238 of the elongate device 231 and (ii) independent "left-right" steering of the elongate device 231 to control a yaw of the distal portion 238 of the elongate device 231.

The medical instrument 232 of the medical instrument system 204 can be used for medical procedures, such as for survey of anatomical passageways, surgery, biopsy, ablation, illumination, irrigation, and/or suction. Thus, the medical instrument 232 can include image capture probes, biopsy instruments, laser ablation fibers, and/or other surgical, diagnostic, and/or therapeutic tools. For example, the medical instrument 232 can include an endoscope having one or more image capture devices 247 positioned at a distal portion 237 of and/or at other locations along the medical instrument 232. In these embodiments, the image capture device 247 can capture one or more real images or video (e.g., a sequence of one or more real navigation image frames) of anatomic passageways and/or other patient anatomy while the medical instrument 232 is within the anatomic region of the patient 203.

As discussed above, the medical instrument 232 can be deployed into and/or be delivered to a target location within the patient 203 via the channel 244 defined by the elongate device 231. In embodiments in which the medical instrument 232 includes an endoscope or other medical device having the image capture device 247 at the distal portion 237 of the medical instrument 232, the image capture device 247 can be advanced to the distal portion 238 of the elongate device 231 before, during, and/or after the manipulator assembly 202 navigates the distal portion 238 of the elongate device 231 to a target location within the patient 203. In these embodiments, the medical instrument 232 can be used as a survey instrument to capture real images and/or video of anatomic passageways and/or other patient anatomy, and/or to aid the operator (e.g., a physician) to navigate the distal portion 238 of the elongate device 231 through anatomic passageways to the target location.

As another example, after the manipulator assembly 202 positions the distal portion 238 of the elongate device 231 proximate a target location within the patient 203, the medical instrument 232 can be advanced beyond the distal portion 238 of the elongate device 231 to perform a medical procedure at the target location. Continuing with the above example, after all or a portion of the medical procedure at the target location is complete, the medical instrument 232 can be retracted back into the elongate device 231 and, additionally or alternatively, be removed from the proximal end 236 of the elongate device 231 or from another instrument port (not shown) along the elongate device 231.

In the example embodiment shown in FIG. 7, the sensor system 208 of the medical instrument system 204 includes a shape sensor 233 and a position measuring device 239. In some embodiments, the sensor system 208 includes all or a portion of the sensor system 108 of FIG. 6. In these and other embodiments, the shape sensor 233 of the sensor system 208 includes an optical fiber extending within and aligned with the elongate device 231. In one embodiment, the optical fiber of the shape sensor 233 has a diameter of approximately 200 μm. In other embodiments, the diameter of the optical fiber may be larger or smaller.

The optical fiber of the shape sensor 233 forms a fiber optic bend sensor that is used to determine a shape of the elongate device 231. In some embodiments, optical fibers having Fiber Bragg Gratings (FBGs) can be used to provide strain measurements in structures in one or more dimensions. Various systems and methods for monitoring the shape and relative position of an optical fiber in three dimensions are described in further detail in U.S. Patent Application Publication No. 2006-0013523 (filed Jul. 13, 2005) (disclosing fiber optic position and shape sensing device and method relating thereto); U.S. Pat. No. 7,781,724 (filed on Sep. 26, 2006) (disclosing fiber-optic position and shape sensing device and method relating thereto); U.S. Pat. No. 7,772,541 (filed on Mar. 12, 2008), (disclosing fiber-optic position and/or shape sensing based on Rayleigh scatter); and U.S. Pat. No. 6,389,187 (filed on Jun. 17, 1998) (disclosing optical fiber bend sensor), which are all incorporated by reference herein in their entireties. In these and other embodiments, sensors of the disclosed technology may employ other suitable strain sensing techniques, such as Rayleigh scattering, Raman scattering, Brillouin scattering, and Fluorescence scattering. In these and still other embodiments, the shape of the elongate device 231 may be determined using other techniques. For example, a history of the pose of the distal portion 238 of the elongate device 231 can be used to reconstruct the shape of elongate device 230 over an interval of time.

In some embodiments, the shape sensor 233 is fixed at a proximal point 234 on the instrument body 235 of the medical instrument system 204. In operation, for example, the shape sensor 233 measures a shape in the medical instrument reference frame ($X_M$, $Y_M$, $Z_M$) from the proximal point 234 to another point along the optical fiber, such as the distal portion 238 of the elongate device 231. The proximal point 234 of the shape sensor 233 may be movable along with instrument body 235 but the location of proximal point 234 may be known (e.g., via a tracking sensor or other tracking device).

The position measuring device 239 of the sensor system 208 provides information about the position of the instrument body 235 as it moves along the insertion axis A on the insertion stage 228 of the manipulator assembly 202. In some embodiments, the position measuring device 239 includes resolvers, encoders, potentiometers, and/or other sensors that determine the rotation and/or orientation of actuators (not shown) controlling the motion of the instrument carriage 226 of the manipulator assembly 202 and, consequently, the motion of the instrument body 235 of the medical instrument system 204.

Figure 8:
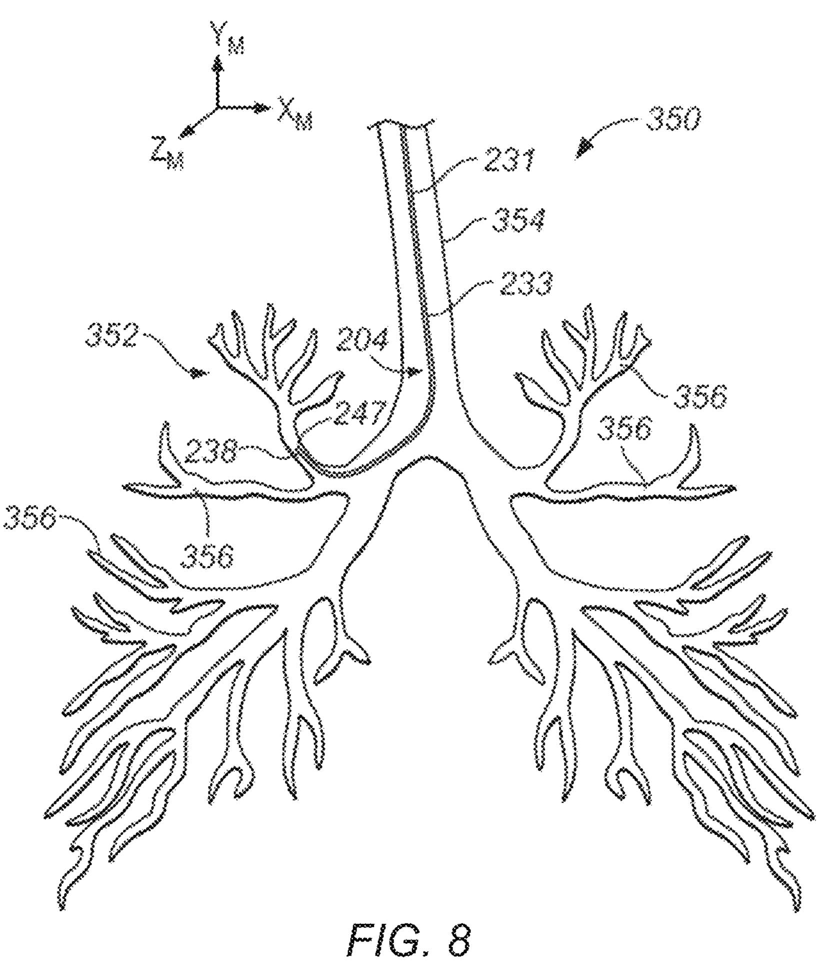
FIG. 8 is an illustrative diagram of a portion of the medical instrument system of FIG. 7 extended within an anatomic region of a patient in accordance with various embodiments of the present technology.

FIG. 8 is a schematic representation of a portion of the medical instrument system 204 of FIG. 7 extended within an anatomic region 350 (e.g., human lungs) of the patient 203 in accordance with various embodiments of the disclosed technology. In particular, FIG. 8 illustrates the elongate device 231 of the medical instrument system 204 extending within branched anatomic passageways 352 of the anatomic region 350. The anatomic passageways 352 include a trachea 354 and bronchial tubes 356.

As shown in FIG. 8, the elongate device 231 has a position, orientation, pose, and shape within the anatomic region 350, all or a portion of which (in addition to or in lieu of movement, such as speed or velocity) can be captured by the shape sensor 233 and/or the position measuring device 239 of the sensor system 208 to survey the anatomic passageways 352 of the anatomic region 350. In particular, the shape sensor 233 and/or the position measuring device 239 of the sensor system 208 can survey the anatomic passageways 352 by gathering positional information of the medical instrument system 204 within the anatomic region 350 in the medical instrument frame of reference ($X_M$, $Y_M$, $Z_M$). The positional information may be recorded as a set of two-dimensional or three-dimensional coordinate points. In the example of the anatomic region 350 being human lungs, the coordinate points may represent the locations of the distal portion 238 of the elongate device 231 and/or other portions of the elongate device 231 while the elongate device 231 is advanced through the trachea 354 and the bronchial tubes 356. In these and other embodiments, the collection of coordinate points may represent the shape(s) of the elongate device 231 while the elongate device 231 is advanced through the anatomic region 350. In these and other embodiments, the coordinate points may represent positional data of other portions (e.g., the medical instrument 232) of the medical instrument system 104.

Figure 9:
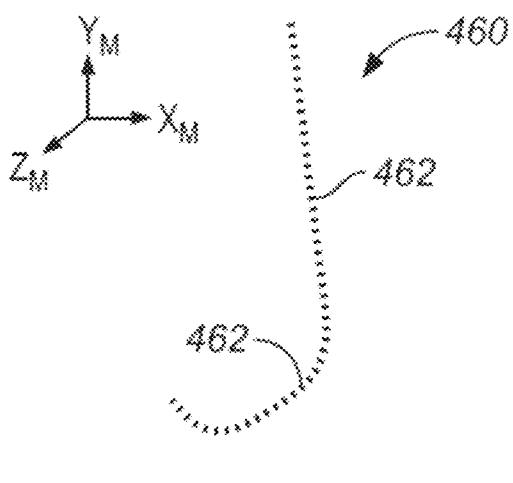
FIG. 9 is a diagram illustrating a plurality of coordinate points that form a point cloud representing a shape of the portion of the medical instrument system of FIG. 8 extended within the anatomic region shown in FIG. 8.

The coordinate points may together form positional point cloud data. For example, FIG. 9 illustrates a plurality of coordinate points 462 forming positional point cloud data 460 representing a shape of the elongate device 231 while the elongate device 231 is within the anatomic region 350 (previously shown in FIG. 8) in accordance with various embodiments of the disclosed technology. In particular, the positional point cloud data 460 is generated from the union of all or a subset of the recorded coordinate points 462 of the shape sensor 233 (previously shown in FIGS. 7 and 8) and/or of the position measuring device 239 (previously shown in FIG. 7) during a data acquisition period by the sensor system 208. The positional point cloud data 460 can be updated by implementation of the example embodiments in accordance with the disclosed methods, systems, devices and computer program products.

In some embodiments, a point cloud (e.g., the point cloud 460) can include the union of all or a subset of coordinate points recorded by the sensor system 208 during an image capture period that spans multiple shapes, positions, orientations, and/or poses of the elongate device 231 within the anatomic region 350. In these embodiments, the point cloud can include coordinate points captured by the sensor system 208 that represent multiple shapes of the elongate device 231 while the elongate device 231 is advanced or moved through patient anatomy during the image capture period. Additionally, or alternatively, because the configuration, including shape and location, of the elongate device 231 within the patient 203 may change during the image capture period due to anatomical motion, the point cloud in some embodiments can comprise a plurality of coordinate points 462 captured by the sensor system 208 that represent the shapes of the elongate device 231 as the elongate device 231 passively moves within the patient 203. A point cloud of coordinate points captured by the sensor system 208 can be registered to different models or datasets of patient anatomy. For example, the positional point cloud data 460 can be used in registration with different models of the branched anatomic passageways 352.

Referring again to FIG. 7, the endoscopic imaging system 209 of the medical instrument system 204 includes one or more image capture devices configured to capture one or more images and/or video (e.g., a sequence of image frames) of anatomic passageways (e.g., the anatomic passageways 352 of FIG. 8) and/or other patient anatomy while the elongate device 231 and/or the medical instrument 232 is within the patient 203. For example, the endoscopic imaging system 209 can include (i) the image capture device 247 positioned at the distal portion 237 of the medical device 232 and/or (ii) one or more other image capture devices (not shown) positioned at other locations along the medical device 232. In these and other embodiments, the endoscopic imaging system 209 can include one or more image capture devices (not shown) positioned at the distal portion 238 and/or other locations along the elongate device 231. In some embodiments, the endoscopic imaging system 209 can include all or a portion of the endoscopic imaging system 109 of FIG. 6.

As shown in FIG. 8, the image capture device 247 of the medical instrument 234 is positioned at the distal portion 238 of the elongate device 231. In this embodiment, the image capture device 247 surveys the anatomic passageways 352 by capturing real images of the anatomic passageways 352 while the elongate device 231 is advanced through the trachea 354 and the bronchial tubes 356 of the anatomic region 350.

Figure 10:
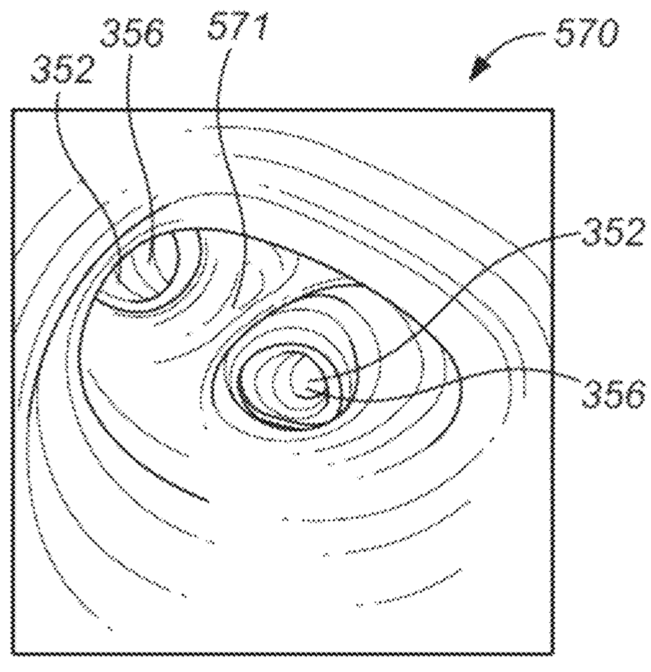
FIG. 10 is a diagram illustrating a navigational image of real patient anatomy from a viewpoint of the portion of the medical instrument system of FIG. 8 extended within the anatomic region shown in FIG. 8.

FIG. 10 is an example of an endoscopic video image frame 570 (e.g., a real image, such as a still image, an image frame of a video, etc.) of patient anatomy of the anatomic region 350 such as the anatomic passageways 352 of FIG. 8 captured using the image capture device 247 of the medical instrument system 204. As shown, the real image 570 illustrates a branching point 571 of two bronchial tubes 356 (within the anatomic region 350 illustrated in FIG. 8) from a viewpoint of the medical instrument 232. In this example, the viewpoint is from the distal tip of the medical instrument 232, such that the medical instrument 232 is not visible within the real image 570. In other embodiments, the image capture device 247 can be positioned at another location along the medical instrument 232 and/or along the elongate device 231 such that the real image 570 is taken from another viewpoint of the medical instrument 232 and/or from another viewpoint of the elongate device 231. A portion of the medical device 232 and/or of the elongate device 231 may be visible within the real image 570 depending on the positions of the medical instrument 232 and the elongate device 231 relative to one another.

Referring again to FIG. 7, the real images captured by the endoscopic imaging system 209 can facilitate navigation of the distal portion 238 of the elongate device 231 through anatomic passageways (e.g., the anatomic passageways 352 of FIG. 8) of the patient 203 and/or delivery of the distal portion 238 of the elongate device 231 to a target location within the patient 203. In these and other embodiments, the real images captured by the endoscopic imaging system 209 can facilitate (i) navigation of the distal portion of the medical instrument 232 beyond the distal portion 238 of the elongate device 231, (ii) delivery of the distal portion of the medical instrument 232 to a target location within the patient 203, and/or (iii) visualization of patient anatomy during a medical procedure. In some embodiments, each real image captured by the endoscopic imaging system 209 can be associated with a time stamp and/or a position within an anatomic region of the patient 203.

As illustrated in FIG. 7, the imaging system 218 can be arranged near the patient 203 to obtain three-dimensional images of the patient 203. In some embodiments, the imaging system 218 includes one or more imaging technologies, including CT, Mill, fluoroscopy, thermography, ultrasound, OCT, thermal imaging, impedance imaging, laser imaging, nanotube X-ray imaging, and/or the like. The imaging system 218 is configured to generate image data of the patient 203 before, during, and/or after the elongate device 231 is extended within the patient 203. Thus, the imaging system 218 can be configured to capture preoperative, intraoperative, and/or postoperative three-dimensional images of the patient 203. In these and other embodiments, the imaging system 218 may provide real-time or near real-time images of the patient 203.

Figure 11:
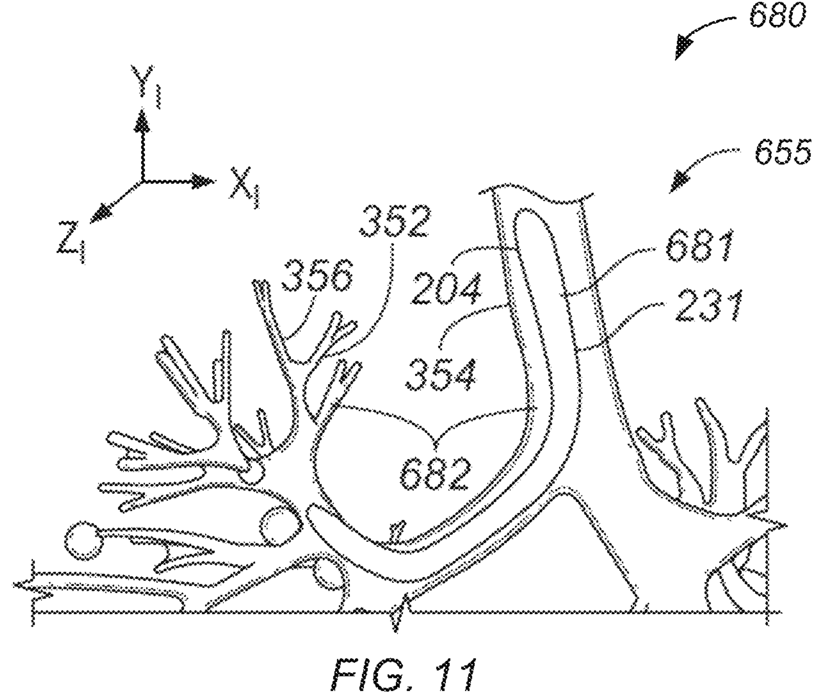
FIG. 11 is a diagram illustrating an intra-operative image of a portion of the anatomic region of FIG. 8 while the portion of the medical instrument system of FIG. 8 is extended within the anatomic region.

FIG. 11 illustrates such intra-operative image data 680 of a portion 655 of the anatomic region 350 of FIG. 8 captured during an image capture period by the imaging system 218 while the elongate device 231 of the medical instrument system 204 is extended within the anatomic region 350. As shown, the image data 680 includes graphical elements 681 representing the elongate device 231 and graphical elements 682 representing the anatomical passageways 352 of the anatomic region 350.

All or a portion of the graphical elements 681 and 682 of the image data 680 can be segmented and/or filtered to generate (i) a three-dimensional model of the anatomical passageways 352 of the portion 655 of the anatomic region 350, and/or (ii) an image point cloud of the elongate device 231 within the anatomic region 350. During the segmentation process, pixels or voxels generated from the image data 680 may be partitioned into segments or elements or be tagged to indicate that they share certain characteristics or computed properties such as color, density, intensity, and texture. The segments or elements may then be converted to a model and/or a point cloud. Additionally, or alternatively, the segments or elements can be used to locate (e.g., calculate) and/or define a center line running along the anatomical passageways 352. The generated anatomic models and/or point clouds may be two or three-dimensional and may be generated in an image reference frame ($X_I$, $Y_I$, $Z_I$).

As discussed above with respect to FIG. 6, the display system 110 of the medical system 100 can display various images or representations of patient anatomy and/or of the medical instrument system 104 based on data captured and/or generated by the positional sensor system 108, by the endoscopic imaging system 109, by the imaging system 118, and/or by the virtual visualization system 115. In various implementations, the images and/or representations can be utilized by the system to aid the operator 105 in conducting an image-guided medical procedure.

Figure 12:
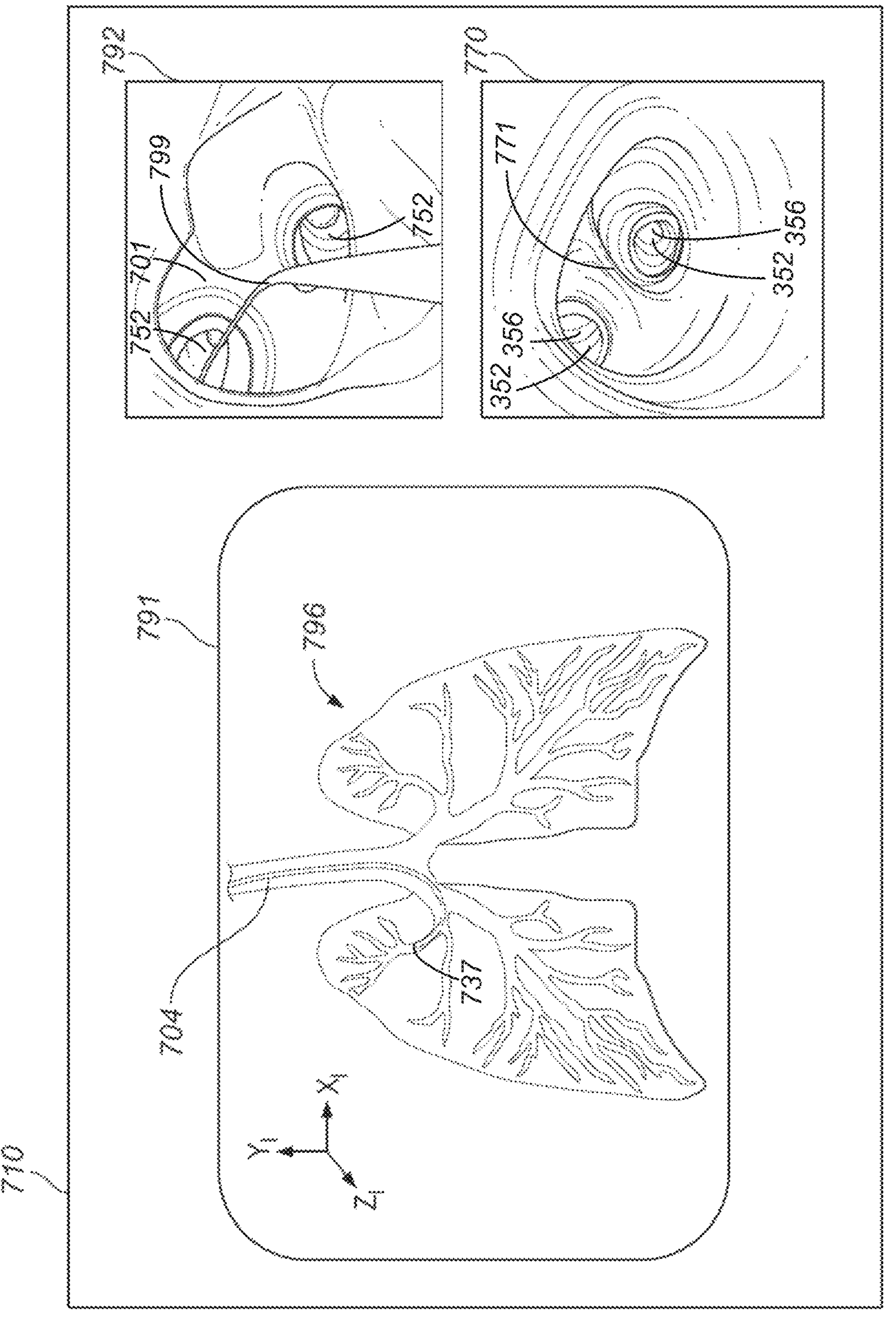
FIG. 12 is a diagram of a display system displaying a composite virtual navigational image in which the medical instrument system of FIGS. 7 and 8 is registered to an anatomic model of the anatomic region of FIG. 8, a virtual navigational image of the virtual patient anatomy, and a real navigational image of the real patient anatomy within the anatomic region in accordance with various embodiments of the present technology.

FIG. 12 is a schematic representation of an example display 710 produced by the display system 110 in accordance with various embodiments of the disclosed technology. As shown, the display 710 includes a real navigational image 770, a composite virtual navigational image 791 (also referred to as "composite virtual image 791"), and a virtual navigational image 792. The real navigational image 770 can be substantially the same as the real navigational image 570 of FIG. 10. Thus, for example, the real navigational image 770 can be captured by the endoscopic imaging system 109 (FIG. 7) and provided to the display system 110 to be presented on the display 710 in real-time or near real-time. In the illustrated embodiment, the real navigational image 770 illustrates real patient anatomy, e.g., such as a real image of a branching point or carina 771 at which an anatomic passageway branches into the two bronchial tubes 356 and/or anatomic passageways 352) from a viewpoint oriented distally away from the distal portion 237 of the medical instrument 232.

The composite virtual image 791 of FIG. 12 is displayed in the image reference frame ($X_I$, $Y_I$, $Z_I$) and includes an anatomic model 796 generated from image data (e.g., of the anatomic region 350 of FIG. 8) captured by the imaging system 118. The anatomic model 796 is registered (i.e., dynamically referenced) with a point cloud of coordinate points (e.g., the point cloud 460 of FIG. 9) generated by the positional sensor system 108 to display a representation 704 within the anatomic model 796 of the tracked position, shape, pose, orientation, and/or movement of embodiments of the medical instrument system 104 (e.g., such as of the elongate device 231 of FIG. 7) within the patient 103. In some embodiments, the composite virtual image 791 is generated by the virtual visualization system 115 (FIG. 6) of the control system 112 (FIG. 6). Generating the composite virtual image 791 involves registering the image reference frame ($X_I$, $Y_I$, $Z_I$) with the surgical reference frame ($X_S$, $Y_S$, $Z_S$) and/or to the medical instrument reference frame ($X_M$, $Y_M$, $Z_M$). This registration may rotate, translate, or otherwise manipulate by rigid and/or non-rigid transforms coordinate points of the point cloud (e.g., the coordinate points 462 of the point cloud 460 of FIG. 9) captured by the positional sensor system 108 to align the coordinate points with the anatomic model 796. The registration between the image and surgical/instrument frames of reference may be achieved, for example, by using a point-based iterative closest point (ICP) technique as described in U.S. Provisional Pat. App. Nos. 62/205,440 and No. 62/205,433, which are both incorporated by reference herein in their entireties. In other embodiments, the registration can be achieved using another point cloud registration technique.

Based at least in part on the registration, the virtual visualization system 115 can additionally or alternatively generate virtual navigational images (e.g., the virtual navigational image 792) that include a virtual depiction of patient anatomy from a viewpoint of a virtual camera on the representation 704 of the medical instrument system 104 (FIG. 9) within the anatomic model 796. In the embodiment illustrated in FIG. 12 of the representation 704 of the medical instrument system 204 shown in FIG. 7, the virtual camera is positioned at the distal portion 737 of representation 704 (e.g., of the medical instrument 232) such that (i) the viewpoint of the virtual navigational image 792 (shown in FIG. 12) is directed distally away from the distal portion 737 of the representation 704 and (ii) the representation 704 is not visible within the virtual navigational image 792. In other embodiments, the virtual visualization system 115 can position the virtual camera (i) at another location along the representation 704 and/or (ii) in a different orientation such that the virtual navigational image 792 has a corresponding virtual viewpoint. In some embodiments, depending on the position and orientation of the virtual camera and the positions of the elongate device 231 and the medical instrument 232 relative to one another when within the patient 103, the virtual visualization system 115 can render a virtual representation (not shown) of at least a portion of the elongate device 231 and/or of the medical instrument 232 into the virtual navigational image 792.

In some embodiments, the virtual navigational image 792 can optionally include a navigation stripe 799. In some implementations, for example, the navigation stripe 799 is used to aid the operator 105 to navigate the medical instrument system 104 through anatomic passageways to a target location within a patient 103. For example, the navigation stripe 799 can illustrate a "best" path through patient anatomy for the operator 105 to follow to deliver the distal portions 237 and/or 238 of the medical instrument 232 and/or of the elongate device 231, respectively, to a target location within an anatomic region. In some embodiments, the navigation stripe 799 can be aligned with a centerline of or another line along (e.g., the floor of) a corresponding anatomic passageway.

In some embodiments, the virtual visualization system 115 can place the virtual camera within the anatomic model 796 at a position and orientation corresponding to the position and orientation of the image capture device 247 within the patient 103. As further shown in FIG. 12, the virtual navigational image 792 illustrates virtual patient anatomy from substantially the same location at which the real navigational image 770 is captured by the image capture device 247, e.g., showing carina 701 marking a branching point of two anatomic passageways 752 of the anatomic model 796. Thus, the virtual navigational image 792 provides a rendered estimation of patient anatomy visible to the image capture device 247 at a given location within the anatomic region 350 of FIG. 8. Because the virtual navigational image 792 is based on the registration of a point cloud generated by the positional sensor system 108 and image data captured by the imaging system 118, the correspondence between the virtual navigational image 792 and the real navigational image 770 provides insight regarding the accuracy and/or efficiency of the registration and can be used to improve the registration. Furthermore, the real navigational images (e.g., the real navigational images 570 and 770) captured by the endoscopic imaging system 109 can (a) provide information regarding the position and orientation of the medical instrument system 104 within the patient 103, (b) provide information regarding portions of an anatomic region actually visited by the medical instrument system, and/or (c) help identify patient anatomy (e.g., branching points or carinas of anatomic passageways) proximate the medical instrument system 104, any one or more of which can be used to improve the accuracy and/or efficiency of the registration.

C. Examples

Several aspects of the present technology are set forth in the following examples. Although several aspects of the present technology are set forth in examples directed to systems, computer-readable mediums, and methods, any of these aspects of the present technology can similarly be set forth in examples directed to any of systems, computer-readable mediums, and methods in other embodiments.

1. A system for providing real-time three-dimensional (3D) image information from an imaging system to a medical device, the system comprising:
   - a processor of a computing device; and
   - a memory of the computing device coupled to the processor and storing instructions that, when executed by the processor, cause the system to perform operations comprising:
     - receiving, at the computing device, video data comprising a plurality of image frames sampled from a 3D volume data set of an imaged anatomical region of a patient displayable on a monitor, wherein the plurality of image frames correspond to a plurality of volume data reconstruction images displayed on the monitor in a series of image slices of a scrollable image stack;
     - implementing an optical character recognition (OCR) technique on the plurality of image frames to render text information contained in the image frames;
     - analyzing the rendered text information to identify a constant text feature that is the same in each of the image frames and a varying text feature that is different in each of the image frames;
     - evaluating the varying text feature in each of the image frames to create an ordered set of the image frames sorted according to a sequence based on a value of each evaluated varying text feature; and
   - producing processed video data comprising the ordered set of the image frames.

2. The system of example 1 wherein the operations further comprise verifying that the ordered set of the image frames is organized according to the series of image slices of the scrollable image stack by allowing the user to view the processed video data on a display screen.

3. The system of example 1 or example 2 wherein the operations further comprise providing the processed video data to a point cloud processing module of the medical device to process the image frames and extract information used in a navigation data point cloud for the medical device.

4. The system of any one of examples 1-3 wherein the operations further comprise sampling each image of the plurality of volume data reconstruction images to produce the video data as a user scrolls through each image, and wherein the plurality of volume data reconstruction images includes at least one static view that does not change and one scrolling view that changes when the user scrolls between two images of the volume data reconstruction images.

5. The system of any one of examples 1-4 wherein operations further comprise transferring the video data from a computer of the imaging system to the computing device in communication with the medical device, and wherein information contained in the 3D volume data set is received at the computing device without using a Digital Imaging and Communications in Medicine (DICOM) network transfer protocol.

6. The system of any one of examples 1-5 wherein the varying text feature includes one of an x-coordinate value, a y-coordinate value, or a z-coordinate value with respect to a coordinate system in the series of image slices of the scrollable image stack for the imaged anatomical region, and wherein the constant text feature includes another one or other two of the x-coordinate value, the y-coordinate value, and the z-coordinate value.

7. The system of any one of examples 1-6 wherein the varying text feature and the constant text feature is included in metadata presented on the volume data reconstruction images 8. The system of example 7 wherein the metadata comprises one or more of a name or identification associated with the patient, a scanning parameter by the imaging system, or system information of the imaging system.

9. The system of any one of examples 1-8 wherein the analyzing includes implementing a change detection technique on an isolated area of each of the image frames to detect the varying text feature and the constant text feature.

10. The system of any one of examples 1-9 wherein the analyzing compares a present location where the constant text feature and the varying text feature are, respectively, in each image frame to determine whether they each appear in a substantially same location with respect to themselves in the image frame for each of the image frames.

11. The system of any one of examples 1-10 wherein the plurality of volume data reconstruction images correspond to a plurality of multi-planar reconstruction (MPR) visualization views comprising an axial, a sagittal and a coronal cross-sectional view, wherein one of the axial, the sagittal, or the coronal cross-sectional view is a scrolling view.

12. The system of any one of examples 1-11 wherein the imaging system includes a CT system or a Cone Beam CT system, and wherein the medical device comprises a sensor, and further wherein the medical device is insertable in an anatomic passageway of the patient.

13. The system of example 12 wherein the sensor of the medical device is configured to generate one or both of position sensor data and motion sensor data during data sampling of the anatomic passageway of the patient's anatomy, and wherein the operations further comprise:

generating a point cloud of coordinate points based at least in part on the one or both of the position sensor data and the motion sensor data, generating a registration between at least a portion of the point cloud and at least a portion of a pre-operative image of the anatomical region, extracting data from the ordered set of image frames in the processed video data to produce coordinate points associated with the imaged anatomical region by the imaging system, and updating the registration based, at least in part, on the produced coordinate points associated with the imaged anatomical region.

14. A system for providing real-time three-dimensional (3D) image information from an imaging system to a medical device, the system comprising:

a processor of a computing device; and a memory of the computing device coupled to the processor and storing instructions that, when executed by the processor, cause the system to perform operations comprising:

receiving, at the computing device, video data comprising a plurality of image frames sampled from a 3D volume data set of an imaged anatomical region of a patient displayable on a monitor, wherein the plurality of image frames correspond to a plurality of volume data reconstruction images displayed on the monitor in a series of image slices of a scrollable image stack;

analyzing the plurality of image frames to detect one or more image features that are characteristic of a static view region in each image frame where planar coordinates associated with the imaged anatomical region remain constant for each image slice in the series of image slices of the scrollable image stack;

evaluating the detected one or more image features to determine a relative location of the detected one or more image features with respect to a scrolling view region for each image frame, wherein the relative location corresponds to at least one of the planar coordinates associated with the imaged anatomical region that varies for each image slice in the series of image slices of the scrollable image stack;

determining an ordered set of the image frames sorted according to a sequence based on relative locations corresponding to the at least one of the planar coordinates that vary in each of the image frames; and producing processed video data comprising the ordered set of the image frames.

15. The system of example 14 wherein the operations further comprise verifying that the ordered set of the image frames is organized according to the series of image slices of the scrollable image stack by allowing the user to view the processed video data on a display screen.

16. The system of example 14 or example 15 wherein the operations further comprise providing the processed video data to a point cloud processing module of the medical device to process the image frames and extract information used in a navigation data point cloud for the medical device.

17. The system of any one of examples 14-16 wherein the operations further comprise sampling each image of the plurality of volume data reconstruction images to produce the video data as a user scrolls through each image, and wherein the plurality of volume data reconstruction images includes at least one static view that does not change and one scrolling view that changes when the user scrolls between two images of the volume data reconstruction images.

18. The system of any one of examples 14-17 wherein the operations further comprise transferring the video data from a computer of the imaging system to the computing device in communication with the medical device, and wherein information contained in the 3D volume data set is received at the computing device without using a Digital Imaging and Communications in Medicine (DICOM) network transfer protocol.

19. The system of any one of examples 14-18 wherein the detected one or more image features includes a line crossing at least a portion of the static view region.

20. The system of any one of examples 14-19 wherein the evaluating the determined one or more image features includes matching a color of the one or more image features between two static view regions in a volume data reconstruction image.

21. The system of any one of examples 14-20 wherein the plurality of volume data reconstruction images correspond to a plurality of multi-planar reconstruction (MPR) visualization views comprising an axial, a sagittal and a coronal cross-sectional view, wherein one of the axial, the sagittal, or the coronal cross-sectional view is a scrolling view.

22. The system of any one of examples 14-21 wherein the imaging system includes a CT system or a Cone Beam CT system, and wherein the medical device comprises a sensor, and further wherein the medical device is insertable in an anatomic passageway of the patient.

23. The system of example 22 wherein the sensor of the medical device is configured to generate one or both of position sensor data and motion sensor data during data sampling of the anatomic passageway of the patient's anatomy, wherein the system is configured to perform further operations that include:

generating a point cloud of coordinate points based at least in part on the one or both of the position sensor data and the motion sensor data, generating a registration between at least a portion of the point cloud and at least a portion of a pre-operative image of the anatomical region, extracting data from the ordered set of image frames in the processed video data to produce coordinate points associated with the imaged anatomical region by the imaging system, and updating the registration based, at least in part, on the produced coordinate points associated with the imaged anatomical region.

24. The system of any one of examples 14-23 wherein the operations further comprise, after determining the ordered set of the image frames, validating the ordered set of the image frames by re-analyzing the plurality of image frames based on a text-recognition technique, and wherein re-analyzing the plurality of image frames comprises:

implementing an optical character recognition (OCR) technique on the plurality of image frames to render text information contained in the image frames, analyzing the rendered text information to identify a constant text feature that is the same in each of the image frames and a varying text feature that is different in each of the image frames, and evaluating the varying text feature in each of the image frames to create a second ordered set of the image frames is sorted according to a sequence based on a value of each evaluated varying text feature; and comparing the ordered set of the image frames to the second ordered set of the image frames.

25. A system for providing real-time three-dimensional (3D) image information from an imaging system to a medical device, the system comprising:

a processor; and a memory coupled to the processor and storing instructions that, when executed by the processor, cause the system to perform operations comprising:

sampling a plurality of image frames from a 3D volume data set of an imaged anatomical region of a patient displayable on a monitor, wherein the 3D volume data set is displayable as a plurality of volume data reconstruction images in a series of image slices of a scrollable image stack;

analyzing a partial region within each of the sampled image frames corresponding to the image slices of the scrollable image stack to identify one or more image features within the analyzed partial region;

determining whether the one or more image features identified in the partial region changes or remains constant for each of the sampled image slices;

assigning an index number to a first image frame of the sampled image frames that is different than an index number assigned to a second image frame of the sampled image frames when it is determined that the identified one or more image features has changed with respect to the first image frame and the second image frame; and producing an ordered set of the sampled image frames based on the assigned index number to create pseudo volume image data.

D. Conclusion

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. Furthermore, the various embodiments described herein can also be combined to provide further embodiments.

Implementations of the subject matter and the functional operations described in this patent document can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and both A and B. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded.

Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

From the foregoing, it will also be appreciated that various modifications can be made without deviating from the technology. For example, various components of the technology can be further divided into subcomponents, or various components and functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A system for providing real-time three-dimensional (3D) image information from an imaging system to a medical device, the system comprising:

a processor of a computing device; and a memory of the computing device coupled to the processor and storing instructions that, when executed by the processor, cause the system to perform operations comprising:

receiving, at the computing device, video data comprising a plurality of image frames sampled from a 3D volume data set of an imaged anatomical region of a patient displayable on a monitor, wherein the plurality of image frames correspond to a plurality of volume data reconstruction images displayed on the monitor in a series of image slices of a scrollable image stack;

analyzing the plurality of image frames to detect one or more image features that are characteristic of a static view region in each image frame where planar coordinates associated with the imaged anatomical region remain constant for each image slice in the series of image slices of the scrollable image stack;

evaluating the detected one or more image features to determine a relative location of the detected one or more image features with respect to a scrolling view region for each image frame, wherein the relative location corresponds to at least one of the planar coordinates associated with the imaged anatomical region that varies for each image slice in the series of image slices of the scrollable image stack;

determining an ordered set of the image frames sorted according to a sequence based on relative locations corresponding to the at least one of the planar coordinates that vary in each of the image frames; and producing processed video data comprising the ordered set of the image frames.

2. The system of claim 1 wherein the operations further comprise verifying that the ordered set of the image frames is organized according to the series of image slices of the scrollable image stack by allowing a user to view the processed video data on a display screen.

3. The system of claim 1 wherein the operations further comprise providing the processed video data to a point cloud processing module of the medical device to process the image frames and extract information used in a navigation data point cloud for the medical device.

4. The system of claim 1 wherein the operations further comprise sampling each image of the plurality of volume data reconstruction images to produce the video data as a user scrolls through each image, and wherein the plurality of volume data reconstruction images includes at least one static view that does not change and one scrolling view that changes when the user scrolls between two images of the volume data reconstruction images.

5. The system of claim 1 wherein the operations further comprise transferring the video data from a computer of the imaging system to the computing device in communication with the medical device, and wherein information contained in the 3D volume data set is received at the computing device without using a Digital Imaging and Communications in Medicine (DICOM) network transfer protocol.

6. The system of claim 1 wherein the detected one or more image features includes a line crossing at least a portion of the static view region.

7. The system of claim 1 wherein the evaluating the detected one or more image features includes matching a color of the one or more image features between two static view regions in a volume data reconstruction image.

8. The system of claim 1 wherein the plurality of volume data reconstruction images correspond to a plurality of multi-planar reconstruction (MPR) visualization views comprising an axial, a sagittal and a coronal cross-sectional view, wherein one of the axial, the sagittal, or the coronal cross-sectional view is a scrolling view.

9. The system of claim 1 wherein the imaging system includes a CT system or a Cone Beam CT system, and wherein the medical device comprises a sensor, and further wherein the medical device is insertable in an anatomic passageway of the patient.

10. The system of claim 9 wherein the sensor of the medical device is configured to generate one or both of position sensor data and motion sensor data during data sampling of the anatomic passageway of the patient, wherein the system is configured to perform further operations that include:

generating a point cloud of coordinate points based at least in part on the one or both of the position sensor data and the motion sensor data, generating a registration between at least a portion of the point cloud and at least a portion of a pre-operative image of the anatomical region, extracting data from the ordered set of the image frames in the processed video data to produce coordinate points associated with the imaged anatomical region by the imaging system, and updating the registration based, at least in part, on the produced coordinate points associated with the imaged anatomical region.

11. The system of claim 9 wherein the sensor of the medical device is configured to generate one or both of position sensor data and motion sensor data during data sampling of the anatomic passageway of the patient, wherein the system is configured to perform further operations that include:

generating a point cloud of coordinate points based at least in part on the one or both of the position sensor data and the motion sensor data, generating a registration between at least a portion of the point cloud and at least a portion of a pre-operative image of the anatomical region, extracting data from the ordered set of the image frames to produce coordinate points associated with the imaged anatomical region by the imaging system, and updating the registration based, at least in part, on the produced coordinate points associated with the imaged anatomical region.

12. The system of claim 1 wherein the operations further comprise, after determining the ordered set of the image frames, validating the ordered set of the image frames by re-analyzing the plurality of image frames based on a text-recognition technique, and wherein re-analyzing the plurality of image frames comprises:

implementing an optical character recognition (OCR) technique on the plurality of image frames to render text information contained in the image frames, analyzing the rendered text information to identify a constant text feature that is the same in each of the image frames and a varying text feature that is different in each of the image frames, evaluating the varying text feature in each of the image frames to create a second ordered set of the image frames is sorted according to a sequence based on a value of each evaluated varying text feature, and comparing the ordered set of the image frames to the second ordered set of the image frames.

13. A system for providing real-time three-dimensional (3D) image information from an imaging system to a medical device, the system comprising:

a processor; and a memory coupled to the processor and storing instructions that, when executed by the processor, cause the system to perform operations comprising:

sampling a plurality of image frames from a 3D volume data set of an imaged anatomical region of a patient displayable on a monitor, wherein the 3D volume data set is displayable as a plurality of volume data reconstruction images in a series of image slices of a scrollable image stack;

analyzing a partial region within each of the sampled image frames corresponding to the image slices of the scrollable image stack to identify one or more image features within the analyzed partial region;

determining whether the one or more image features identified in the partial region changes or remains constant for each of the sampled image frames;

assigning an index number to a first image frame of the sampled image frames that is different than an index number assigned to a second image frame of the sampled image frames when it is determined that the identified one or more image features has changed with respect to the first image frame and the second image frame; and producing an ordered set of the sampled image frames based on the assigned index number to create pseudo volume image data.

14. The system of claim 13 wherein the operations further comprise verifying that the ordered set of the sampled image frames is organized according to the series of image slices of the scrollable image stack by allowing a user to view the pseudo volume image data on a display screen.

15. The system of claim 13 wherein the operations further comprise providing the pseudo volume image data to a point cloud processing module of the medical device to process the sampled image frames and extract information used in a navigation data point cloud for the medical device.

16. The system of claim 13 wherein the operations further comprise sampling each image of the plurality of volume data reconstruction images to produce the pseudo volume image data as a user scrolls through each image, and wherein the plurality of volume data reconstruction images includes at least one static view that does not change and one scrolling view that changes when the user scrolls between two images of the volume data reconstruction images.

17. The system of claim 13 wherein the identified one or more image features includes a line crossing at least a portion of the analyzed partial region.

18. The system of claim 13 wherein the determining whether the one or more image features changes or remains constant includes matching a color of the one or more image features between two static view regions in a volume data reconstruction image.

19. The system of claim 13 wherein the plurality of volume data reconstruction images correspond to a plurality of multi-planar reconstruction (MPR) visualization views comprising an axial, a sagittal and a coronal cross-sectional view, wherein one of the axial, the sagittal, or the coronal cross-sectional view is a scrolling view.

20. The system of claim 13 wherein the imaging system includes a CT system or a Cone Beam CT system, and wherein the medical device comprises a sensor, and further wherein the medical device is insertable in an anatomic passageway of the patient.

* * * * *